(12) United States Patent
Lin et al.

(10) Patent No.: US 9,999,636 B2
(45) Date of Patent: *Jun. 19, 2018

(54) INSULIN-MIMETICS AS THERAPEUTIC ADJUNCTS FOR BONE REGENERATION

(71) Applicant: Rutgers, The State University of New Jersey, New Brunswick, NJ (US)

(72) Inventors: Sheldon S. Lin, Chatham, NJ (US); David N. Paglia, Wayland, MA (US); James P. O'Connor, Fanwood, NJ (US); Joseph Benevenia, Montclair, NJ (US); Aaron Wey, East Brunswick, NJ (US); Sangeeta Subramanian, Jacksonville, FL (US); John Koerner, Newark, NJ (US); Paul Chirichella, Fair Lawn, NJ (US); Michael J. Vives, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/010,332

(22) Filed: Jan. 29, 2016

(65) Prior Publication Data
US 2016/0151416 A1 Jun. 2, 2016

Related U.S. Application Data

(60) Division of application No. 14/469,549, filed on Aug. 26, 2014, now Pat. No. 9,265,794, which is a (Continued)

(51) Int. Cl.
*A61K 33/32* (2006.01)
*A61F 2/44* (2006.01)
(Continued)

(52) U.S. Cl.
CPC .......... *A61K 33/32* (2013.01); *A61B 17/7061* (2013.01); *A61F 2/4455* (2013.01);
(Continued)

(58) Field of Classification Search
None
See application file for complete search history.

(56) References Cited

U.S. PATENT DOCUMENTS

| 3,915,151 A | 10/1975 | Kraus |
| 4,878,915 A | 11/1989 | Brantigan |

(Continued)

FOREIGN PATENT DOCUMENTS

| CN | 1511595 A | * | 7/2004 |
| DE | 10238161 A1 | | 2/2004 |

(Continued)

OTHER PUBLICATIONS

Slappey et al., Guidelines to decortication in posterolateral spine fusion., J Spinal Disord. Apr. 1998;11(2):102-9.*

(Continued)

*Primary Examiner* — Carlos A Azpuru
*Assistant Examiner* — Casey S Hagopian
(74) *Attorney, Agent, or Firm* — Fox Rothschild LLP

(57) ABSTRACT

Methods of promoting bone healing or regeneration by locally administering insulin mimetic agents to patients in need thereof and new uses of insulin-mimetic compounds for accelerating bone-healing processes are disclosed. Bone injury treatment and void filler devices, products and kit suitable for local administration of insulin-mimetic, agents or compositions thereof to patients in need of such treatment are also disclosed.

6 Claims, 12 Drawing Sheets

Related U.S. Application Data continuation of application No. 14/359,827, filed as application No. PCT/US2012/067087 on Nov. 29, 2012, which is a continuation-in-part of application No. PCT/US2011/064240, filed on Mar. 18, 2011.

(60) Provisional application No. 61/718,646, filed on Oct. 25, 2012, provisional application No. 61/564,822, filed on Nov. 29, 2011, provisional application No. 61/454,061, filed on Mar. 18, 2011, provisional application No. 61/428,342, filed on Dec. 30, 2010, provisional application No. 61/421,921, filed on Dec. 10, 2010.

(51) Int. Cl.
| | |
|---|---|
| *A61L 27/54* | (2006.01) |
| *A61K 31/69* | (2006.01) |
| *A61K 31/315* | (2006.01) |
| *A61K 33/24* | (2006.01) |
| *A61K 33/00* | (2006.01) |
| *A61B 17/70* | (2006.01) |
| *A61K 45/06* | (2006.01) |
| *A61L 31/16* | (2006.01) |
| *A61K 31/28* | (2006.01) |
| *A61K 31/30* | (2006.01) |
| *A61B 17/86* | (2006.01) |
| *A61B 17/58* | (2006.01) |
| *A61K 33/30* | (2006.01) |
| *A61B 17/56* | (2006.01) |

(52) U.S. Cl.
CPC ............ *A61K 31/28* (2013.01); *A61K 31/315* (2013.01); *A61K 31/69* (2013.01); *A61K 33/00* (2013.01); *A61K 33/24* (2013.01); *A61K 33/30* (2013.01); *A61K 45/06* (2013.01); *A61L 27/54* (2013.01); *A61L 31/16* (2013.01); *A61B 17/866* (2013.01); *A61B 2017/561* (2013.01); *A61B 2017/564* (2013.01); *A61F 2002/4475* (2013.01); *A61F 2210/0085* (2013.01); *A61L 2300/414* (2013.01); *A61L 2430/02* (2013.01); *A61L 2430/38* (2013.01)

(56) References Cited

U.S. PATENT DOCUMENTS

| | | | |
|---|---|---|---|
| 5,019,383 A | 5/1991 | Hopp | |
| 5,061,286 A | 10/1991 | Lyle | |
| 5,614,206 A | 3/1997 | Randolph et al. | |
| 5,716,415 A | 2/1998 | Steffee | |
| 5,842,477 A | 12/1998 | Naughton et al. | |
| 5,871,779 A | 2/1999 | Cruz | |
| 6,569,204 B1* | 5/2003 | Aldecoa | A61K 35/16 623/23.51 |
| 6,743,786 B2 | 6/2004 | Uckun et al. | |
| 7,763,582 B2 | 7/2010 | Lin et al. | |
| 8,936,804 B2 | 1/2015 | Lin et al. | |
| 2001/0014662 A1 | 8/2001 | Rueger et al. | |
| 2003/0211170 A1 | 11/2003 | Gho | |
| 2004/0002558 A1* | 1/2004 | McKay | A61K 38/1875 523/115 |
| 2004/0014727 A1 | 1/2004 | Garrett | |
| 2004/0019132 A1 | 1/2004 | Long et al. | |
| 2004/0121025 A1 | 6/2004 | McKee | |
| 2004/0230309 A1 | 11/2004 | DiMauro et al. | |
| 2004/0242953 A1 | 12/2004 | Good | |
| 2005/0079200 A1 | 4/2005 | Rathenow et al. | |
| 2005/0201987 A1 | 9/2005 | Pirhonen et al. | |
| 2006/0036253 A1* | 2/2006 | Leroux | A61B 17/864 623/16.11 |
| 2006/0051397 A1 | 3/2006 | Maier et al. | |
| 2006/0093646 A1 | 5/2006 | Cima et al. | |
| 2006/0183729 A1 | 8/2006 | Uckun | |
| 2007/0027543 A1 | 2/2007 | Gimble et al. | |
| 2007/0073385 A1 | 3/2007 | Schaeffer et al. | |
| 2007/0181433 A1 | 8/2007 | Birdsall et al. | |
| 2007/0196642 A1 | 8/2007 | Feldstein et al. | |
| 2008/0031217 A1 | 2/2008 | Miller et al. | |
| 2008/0069852 A1 | 3/2008 | Shimp et al. | |
| 2008/0248636 A1 | 10/2008 | Olander et al. | |
| 2009/0068285 A1 | 3/2009 | LeGeros et al. | |
| 2009/0104095 A1 | 4/2009 | Morgan et al. | |
| 2009/0214468 A1 | 8/2009 | Lin et al. | |
| 2009/0220566 A1 | 9/2009 | Barralet et al. | |
| 2009/0226534 A1 | 9/2009 | Marchosky | |
| 2009/0298777 A1 | 12/2009 | McKay | |
| 2010/0168854 A1 | 7/2010 | Luers et al. | |
| 2010/0211158 A1 | 8/2010 | Haverty et al. | |
| 2010/0226943 A1 | 9/2010 | Brennan et al. | |
| 2011/0004307 A1 | 1/2011 | Ahn et al. | |
| 2013/0171094 A1 | 7/2013 | Lin et al. | |
| 2014/0044768 A1 | 2/2014 | Lin et al. | |

FOREIGN PATENT DOCUMENTS

| | | |
|---|---|---|
| EP | 1649877 | 9/2005 |
| FR | 2842750 A1 | 1/2004 |
| JP | 03-120257 | 5/1991 |
| JP | 05-140200 | 6/1993 |
| JP | 08-034744 | 2/1996 |
| JP | 2002-138042 A | 5/2002 |
| JP | 2002542802 A | 12/2002 |
| JP | 2007529515 A | 10/2007 |
| JP | 2011512957 A | 4/2011 |
| RU | 2105529 C1 * | 2/1998 |
| WO | 96/36333 A1 | 11/1996 |
| WO | 00/24730 A1 | 5/2000 |
| WO | 2005032466 A2 | 4/2005 |
| WO | 20050032466 A2 | 4/2005 |
| WO | 2007090433 A2 | 8/2007 |
| WO | 2008048647 A1 | 4/2008 |
| WO | 20090068285 A1 | 6/2009 |
| WO | 2009/111300 A2 | 9/2009 |
| WO | 2010114827 A1 | 10/2010 |
| WO | 20100114827 A1 | 10/2010 |
| WO | 2011/088318 A1 | 7/2011 |
| WO | 2012/079024 A2 | 6/2012 |
| WO | 2013082295 A1 | 6/2013 |

OTHER PUBLICATIONS

Navarro et al., Biomaterial in orthopaedics, J R Soc Interface. Oct. 6, 2008; 5(27): 1137-1158.*

Slappey et al., Guidelines to decortication in posterolateral spine fusion., J Spinal Disord. Apr. 1998;11 (2):102-9.*

USC Center for Spinal Surgery, Anterior Lumbar Corpectomy and Fusion & Anterior Thoracic Corpectomy and Fusion, Mar. 20, 2007, accessed online at http://www.uscspine.com/treatment/corpectomy-fusion.cfm.*

USC Center for Spinal Surgery, Anterior Lumbar Corpectomy and Fusion & Anterior Thoracic Corpectomy and Fusion, Mar. 20, 2007, accessed online at http://www.uscspine.com/treatment/posterior-lumbar-fusion.cfm.*

Columbia University Medical Center, Lumbar Fusion and Fixation, Nov. 14, 2010, accessed online at http://www.columbianeurosurgery.org/specialties/spine/procedures/surgical/lumbar-fusion-and-fixation.*

Barrio et al., Vanadium and bone development: putative signaling pathways, Can. J. Physiol. Pharmacol., vol. 84, No. 7, p. 677-686. (Jul. 2006).

Barrio et al. "Potential use of vanadium compounds in therapeutics", Current Medicinal Chemistry 17(31): 3632-3642. (2010).

Cornish, J. et al., Insulin Increases Histomorphometric Indices of Bone Formation In Vivo, Calcif Tissue Intl, 1996, 59:492-495.

Cortizo et al. "Osteogenic activity of vanadyl(IV)-ascorbate complex: Evaluation of its mechanism of action", International Journal of Biochemistry and Cell Biology 38(7): 1171-1180. (2006).

(56) References Cited

OTHER PUBLICATIONS

Facchini et al. "The effects of vanadium treatment on bone in diabetic and non-diabetic rats", BONE 38(3): 368-377. (2006).
Gandhi, A. et al., The Effects of Local Insulin Delivery on Diabetic Fracture Healing, Bone, 2005, pp. 482-490.
Hayao, Ide et al., "Vanadium Promotes Osteogenesis," Health Chemistry, Department of Medicine, Toho University, Omori Medical Center, Toho University [date unknown, cited in office action for Japanese App. 212-549109 on Dec. 25, 2014] (Abstract).
Kagel EM, et al. Current Opinion in Orthopaedics 6(5):7-13, 1995.
Mehdi et al., "Organo-vanadium compounds are potent activators of the protein kinase B signaling pathway and protein tyrosine phosphorylation: Mechanism of insulinomimesis," Arch. Biochem. Biophys., vol. 440, No. 2, p. 158-164. (Aug. 15, 2005).
Makinen, Marvin et al., "Metabolism and Bioenergetics: Structural Origins of the Insulin-mimetic Activity of Bis(acetylacetonato)oxovanadium(IV)" J. Biol. Chem., 2002, vol. 277, pp. 12215-12220.
Arai Michitsugu: "Effects of vanadyl sulfate on osteopenia in streptozotocin-induced diabetic (STZD) rats: Comparison with those of insulin", Folia Pharmacologica Japonica 100(5): 401-414. (1992).
Millard D. J. Wound Care 4(8):343, 1995.
Paglia et al. "The effects of local vanadium treatment on angiogenesis and chondrogenesis during fracture healing", Journal of Orthopaedic Research 30(12): 1971-1978. (2012).
Stuck, Walter G., The Effect of Insulin on the Healing of Experimental Fractures in the Rabbit, J. Bone Joint Surg Am., 1932, 14:109-115.
Wlldemann B, et al. Bone (34):862-868, 2004.
Zhang, Shuang-Qing et al., "Effects on the Bones of Vanadyl Acetylacetonate by Oral Administration: A Comparison Study in Diabetic Rats," J. Bone Miner Metab, (2007), vol. 25, Issue 5, pp. 293-301.
Barrio et al. "Vanadium and bone development: putative signaling pathways", Journal of the All-India Ophthalmological Society 84(7): 677-686. (2006).
Information about Related Patents and Patent Applications, see section 6 of the accompanying Information Disclosure Statement Letter, which concerns Related Patents and Patent Applications.
Kato, Y., "Effect of Vanadate on Cartilege-Matrix Proteoglycan Synthesis in Rabbit Costal Chondrocyte Cultures," The Journal of Cell Biology, (1987), vol. 104, pp. 311-319.
Hamrin et al., "Local effect of vanadate on interstitial glucose and lactate concentrations in human skeletal muscle," Life Sciences (2005), vol. 76, pp. 2329-2338.
Ide et al., "Vanadium promotes osteogenesis" Convention Program Summary of The Japanese Society for Bone and Mineral Research, (2004), vol. 22, p. 171 (Abstract only).
Kishimoto, "Why are not increase of bone density and effect of fracture prevention consistent?" Journal of Osteoporotic Medicine (2005), vol. 4, No. 3, pp. 44-48 (Abstract only).
Wang, et al.: "Zinc-Containing Apatite Layers on External Fixation Rods Promoting Cell Activity", ACTA Biomaterialia, Elsevier, Amsterdam, Mar. 1, 2010, vol. 6, No. 3, pp. 962-968.
Kazuyuki, et al.: "In Vitro Prominent Bone Regeneration by Release Zinc Ion from Zn-Modified Implant", Biochemical and Biophysical Research Communications, vol. 412, No. 2, Jul. 28, 2011 (Jul. 28, 2011), pp. 273-278.
Alvarez, et al.: "Titanium Implants after Alkali Heating Treatment with a [ZN(OH)4] 2-Complex: Analysis of Interfacial Bond Strength Using Push-Out Tests"; Clinical Implant Dentistry and Related Research, 2010, vol. 12, Supp. 1, pp. e114-e125.
Baquer, et al: "Metabolic and Molecular Action of Trigonella Foenum-Graecum (Fenugreek) and Trace Metals in Experimental Diabetic Tissues", J. Biosci., Jun. 2011, pp. 383-396.
Adachi, et al.: "Comparative Study of Insulin-Mimetic Activity of Vanadium and Zinc Complexes", Biomed Res. Trace Elements, 2004, vol. 15, No. 4, pp. 351-354.
Yoshikawa, et al.: "Challenge of Studies on the Development of New Zn Complexes (Zn(opt)2) to Treat Diabetes Mellitus", Metallomics, 2011, vol. 3, pp. 686-692.
Baquer, et al. "Regulation of Glucose Utilization and Lipogenesis in Adipose Tissue of Diabetic and Fat Fed Animals: Effects of Insulin and Manganese", J. Biosci., Mar. 2003, vol. 28, No. 2, pp. 215-221.
Subasinghe, et al.: "The Insulin-Mimetic Action of Mn2+: Involvement of Cyclic Nucleotides and Insulin in the Regulation of Hepatic Hexokinase and Glucokinase", Biochemical Medicine, 1985, vol. 34, pp. 83-92.
Slappey, et al: "Guidelines to Decortication in Posterolateral Spine Fusion", Apr. 1998, J. Spinal Disord., vol. 11, No. 2 (Abstract only).
USC Center for Spinal Surgery; "Anterior Lumbar Corpectomy and Fusion & Anterior Thoracic Corpectomy and Fusion", Mar. 20, 2007. Retrieved from the Internet: <URL:http://www.uscspine,com/treatment/corpectomy-fusion.cfm>.
USC Center for Spinal Surgery; "Posterior Lumbar Fusion (PLF)", Mar. 20, 2007. Retrieved from the Internet: <URL:http://www.uscspine.com/treatment/posterior-lumbar-fusion.cfm>.
Columbia University Medical Center; "Lumbar Fusion and Fixation", Nov. 14, 2010. Retrieved from the Internet <URL:http;//www.columbianeurosurgery.org/specialties/spine/procedures/surgical/lumbar-fusion-and-fixation>.
Raggatt, et al: "Cellular and Molecular Mechanisms of Bone Remodeling", Journal of Biological Chemistry, Aug. 13, 2010, vol. 285, No. 33, pp. 25103-25108.
Kalfas, Iain H.: "Principles of Bone Healing", Neurosurg Focus, Apr. 2001, vol. 10, No. 4, pp. 1-4.

\* cited by examiner

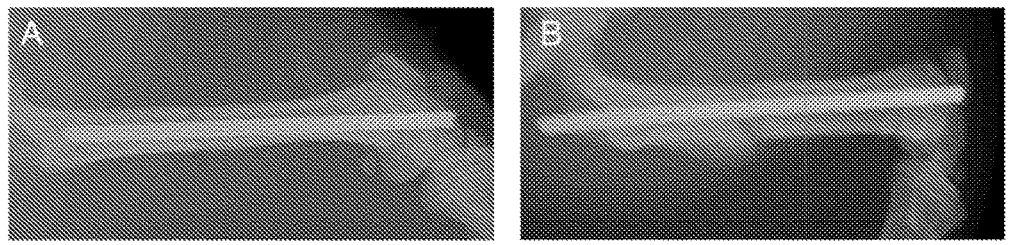
Figure 1
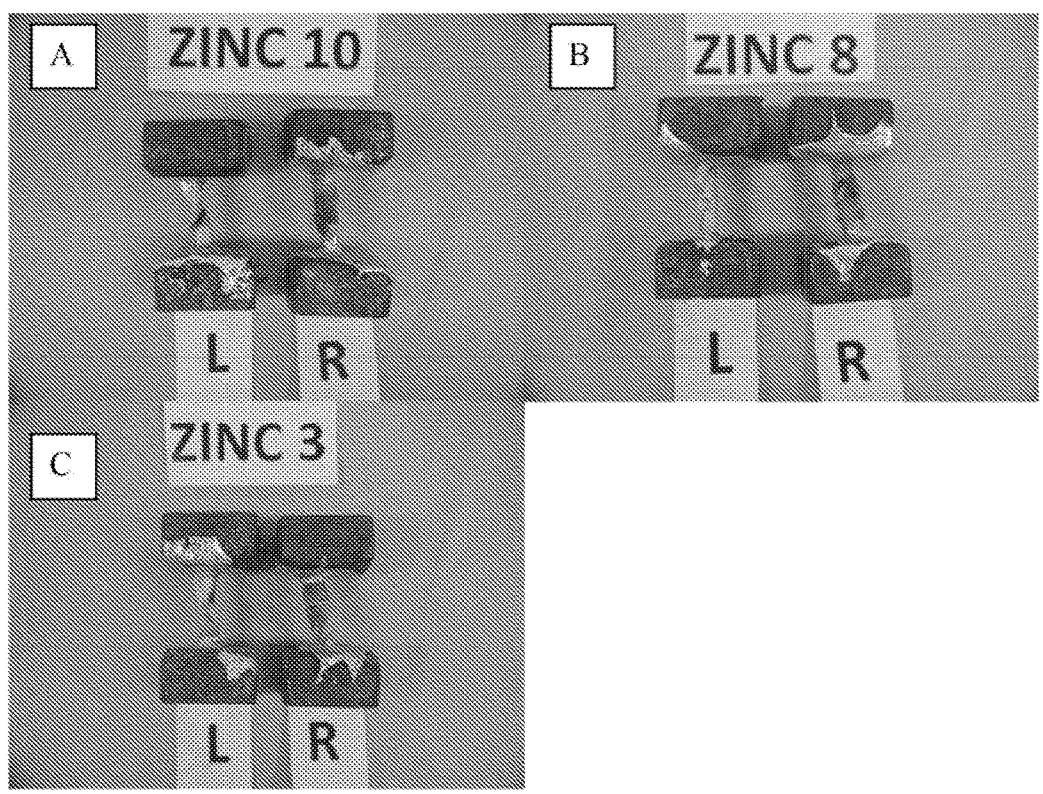
Figures 2 A-C

Anteroposterior view of 4 week
Local MnCl₂ Treated Fractures
Anteroposterior view of 4 week
Saline Control Fractures
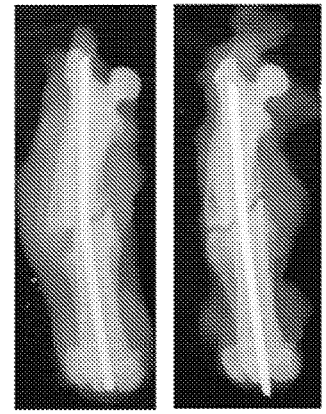
Lateral view of 4 week
Local MnCl₂ Treated Fractures
Lateral view of 4 week
Saline Control Fractures
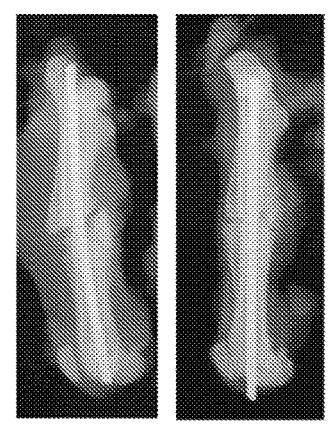
Figure 7

INSULIN-MIMETICS AS THERAPEUTIC ADJUNCTS FOR BONE REGENERATION

CROSS REFERENCE TO RELATED APPLICATIONS

This application is a Divisional Application of U.S. patent application Ser. No. 14/469,549, filed Aug. 26, 2014, which is a Continuation of U.S. patent application Ser. No. 14/359,827, filed May 21, 2014, which is the U.S. National Phase of International Application No. PCT/US12/67087, filed Nov. 29, 2012, which claims priority under 35 U.S.C. § 119(e) to U.S. Provisional Patent Application Ser. No. 61/564,822, filed on Nov. 29, 2011, and No. 61/718,646, filed on Oct. 25, 2012. International Application No. PCT/US12/67087 is a continuation-in-part of International Application No. PCT/US11/64240, filed on Dec. 9, 2011, which in turn claims priority under 35 U.S.C. § 119(e) to U.S. Provisional Patent Application Ser. No. 61/421,921, filed on Dec. 10, 2010, No. 61/428,342, filed on Dec. 30, 2010, and No. 61/454,061, filed on Mar. 18, 2011, all of which are hereby incorporated by reference in their entireties.

FIELD OF THE INVENTION

The present invention relates to use of insulin-mimetic agents as therapeutic adjuncts for bone regeneration and methods for bone healing or regeneration in patients by local administration of insulin-mimetic agents.

BACKGROUND OF THE INVENTION

About six million bone fractures, including about 600,000 non-union cases, occur annually in the United States, among which approximately 10% do not heal. Fracture healing is a complex process that involves the sequential recruitment of cells and the specific temporal expression of factors essential for bone repair. The fracture healing process begins with the initial formation of a blood clot at the fracture site. Platelets and inflammatory cells within the clot release several factors that are important for chemotaxis, proliferation, angiogenesis and differentiation of mesenchymal cells into osteoblasts or chondroblasts.

In the orthopedic procedures conducted, about one million performed annually require allograft or autograft. One solution to enhancement of bone healing is through tissue engineering, in which cells, such as osteoblast, fibroblast, chondroblasts, are treated with bioactive signaling molecules, e.g., insulin or insulin mimetics, with or without a carrier such as β-TCP (CaPO$_4$) and collagen under an appropriate environment. Current methods of treatment of bone fractures include (a) electro-stimulation devices (such as PEMF, Exogen) and (b) biologics, such as bone morphogenic proteins (BMPs), e.g., rhBMP-2/ACS (INFUSE® Bone Graft). The latter has been approved by FDA as an autograft replacement in spine fusion (ALIF) with specific interbody cages (2002), as an adjuvant for repair of tibia fractures with IM nail (2004), and for craniofacial maxillary surgery (2006), but this method is expensive, costing about $5,000 per application. (Lieberman, J. R., et al., *J. Bone Joint Surg. Am.*, 2002, 84: 1032-1044; Trippel, S. B., et al., *J. Bone Joint Surg. Am.*, 1996, 78: 1272-86.)

The fracture healing process subsequent to the initial hematoma formation can be classified as primary or secondary fracture healing. Primary fracture healing occurs in the presence of rigid internal fixation with little to no interfragmentary strain resulting in direct bone formation across the fracture gap. Secondary fracture healing occurs in response to interfragmentary strain due to an absence of fixation or non-rigid fixation resulting in bone formation through intramembranous and endochondral ossification characterized by responses from the periosteum and external soft tissue.

Intramembranous bone formation originates in the periosteum. Osteoblasts located within this area produce bone matrix and synthesize growth factors, which recruit additional cells to the site. Soon after the initiation of intramembranous ossification, the granulation tissue directly adjacent to the fracture site is replaced by cartilage leading to endochondral hone formation. The cartilage temporarily bridging the fracture gap is produced by differentiation of mesenchymal cells into chondrocytes. The cartilaginous callus begins with proliferative chondrocytes and eventually becomes dominated by hypertrophic chondrocytes. Hypertrophic chondrocytes initiate angiogenesis and the resulting vasculature provides a conduit for the recruitment of osteoblastic progenitors as well as chondroclasts and osteoclasts to resorb the calcified tissue. The osteoblastic progenitors differentiate into osteoblasts and produce woven hone thereby firming a united fracture. The final stages of fracture healing are characterized by remodeling of woven bone to form a structure, which resembles the original tissue and has the mechanical integrity of unfractured bone.

However, the processes of bone metabolism are vastly different from bone repair. Bone metabolism is the interplay between bone formation and bone resorption. Bone repair, as described previously, is a complex process that involves the sequential recruitment and the differentiation of mesenchymal cells towards the appropriate osteoblastic/chondrogenic lineage to repair the fracture/defect site.

Spinal fusion is a common procedure performed for a variety of conditions including spondylosis, disk disorders, and spinal stenosis. The rates of pseudoarthrosis after single level spinal fusion have been reported up to 35%. The process of osteogenesis after spinal arthrodesis is similar to that which occurs during fracture healing and heterotopic ossification, and agents that increase the rate of fusion have an important role in decreasing pseudoarthrosis following spinal fusions. To our knowledge, prior to this invention, no in vivo evaluation of therapy on spinal fusion by local administration of an insulin-mimetic agent, such as a zinc or vanadium compound, has been performed.

There is a clear need to develop new methods for repairing bone fractures by enhancing bone regeneration as well as new methods to enhance spinal fusion.

SUMMARY OF THE INVENTION

The present invention provides a unique strategy for bone regeneration through local administration of insulin-mimetic agents, for example, but not limited to, insulin pathway-stimulating zinc, vanadium, tungsten, molybdenum, niobium, selenium, or manganese compounds.

In one aspect the present invention provides a method of treating a bone condition in a patient in need of bone regeneration, comprising locally administering to the patient a therapeutically effective amount of an insulin-mimetic agent.

In another aspect the present invention provides use of an insulin-mimetic compound for manufacture of a medicament for accelerating bone healing or regeneration in a patient in need thereof characterized by local administration of said medicament.

In another aspect the present invention provides a drug delivery device or kit, which includes an insulin-mimetic compound and a pharmaceutically acceptable carrier, wherein the device or kit is adapted for localized administration of the compound to a patient in need thereof.

In another inspect the present invention includes localized administration of an insulin-mimetic compound or a composition thereof in combination with a second method for promoting bone regeneration, selected from bone autograft methods, bone allograft methods, autologous stein cell treatment methods, methods using autologous growth factor concentrates, allogeneic stem cell treatment methods, chemical stimulation methods, electrical stimulation methods, low-intensity pulse ultrasound (LIPUS) methods, internal fixation methods, and external fixation methods.

The present invention also provides a unique strategy to facilitate spinal fusion in spinal fusion procedures.

In one embodiment the present invention provides a bone regeneration material for bone fusion or void filling, comprising an osteoconductive carrier and an insulin-mimetic agent. In one embodiment, the bone regeneration material contains autograft bone tissue. In another embodiment, the bone regeneration material contains allograft bone tissue. In another embodiment, the bone regeneration material contains xenograft bone tissue.

In another aspect the present invention provides a surgical procedure for stabilizing vertebrae in a spine, including the steps of:

exposing a portion of each of adjacent vertebrae; and placing supplementary bone tissue material and an insulin-mimetic agent within an area between the exposed portions of the adjacent vertebrae and in contact with the exposed portions of both vertebrae;

wherein the insulin-mimetic agent is provided in an amount effective to increase the rate of fusion of the two vertebrae with the bone tissue material.

In one embodiment, the vertebrae are lumbar vertebrae. In another embodiment, the vertebrae are cervical vertebrae. In one embodiment, the bone tissue material contains autograft bone tissue. In another embodiment, the bone tissue material contains allograft bone tissue. In one embodiment, the insulin-mimetic agent is mixed with the bone tissue material. In a specific embodiment, the bone tissue material is autograft bone tissue and the insulin-mimetic agent is mixed with the bone tissue material after harvesting and before being placed between the exposed portions of the two vertebrae.

In another embodiment, the method further includes the step of supporting the two vertebrae with a prosthetic implant configured to stabilize the two vertebrae and promote fusion of the two vertebrae with the bone tissue material. In one embodiment, the bone tissue contacting surfaces of the prosthetic implant are coated with the insulin-mimetic agent.

In another aspect, the present invention provides a bone tissue kit for increasing the rate of fusion of vertebrae in a spinal fusion surgical procedure, including the composition containing an insulin-mimetic agent and a pharmaceutically acceptable carrier. In an embodiment the kit also contains allograft bone tissue material. In one embodiment the insulin-mimetic agent and the allograft bone tissue material are provided in a mixture. In another embodiment, the insulin-mimetic agent and allograft bone tissue material are provided for subsequent mixing. In another aspect the present invention provides a composition for increasing the rate of spinal fusion in a spinal fusion surgical procedure, wherein the composition contains an insulin-mimetic agent and a pharmaceutically acceptable carrier. In one embodiment the composition contains allograft bone material In another aspect, the present invention provides an implantable device for enhancing spinal fusion, in which a prosthetic implant is configured to stabilize and promote the fusion of two adjacent vertebrae, wherein the bone tissue contacting surfaces of the prosthetic implant are coated with a composition comprising an insulin-mimetic agent.

Examples of insulin mimetic agents suitable for the present invention include, but are not limited to, insulin pathway-stimulating zinc, vanadium, tungsten, molybdenum, niobium, selenium, and manganese compounds.

The present invention thus provides a unique method for promoting bone healing and enhancing spinal fusion in a patient, preferably mammalian animal and more preferably a human, either diabetic or non-diabetic. Development of an insulin-mimetic therapy of the present invention would obviate the need for developing specialized methods to deliver complex molecules, such as growth factors like insulin, and thereby reduce costs, eliminate specialized storage, and enhance ease of use. These and other aspects of the present invention will be better appreciated by reference to the following drawings and detailed description.

BRIEF DESCRIPTION OF THE DRAWINGS

FIG. 1 depicts post-operative X-rays. Representative x-rays taken immediately post-operative: (A) Einhorn model, (B) model used in this work. (Note in (B) the Kirschner wire is going through the trochanter, which helps to stabilize the fracture site and prevent the migration of the Kirschner wire.)

FIG. 2 depicts Mechanical Testing Setup: Intact femur before embedded in ¾ inch square nut with Field's Metal, where (A) ZINC 10 (3.0 mg/kg ZnCl2) and (B) ZINC 8 (1.0 mg/kg $ZnCl_2$) represent two sets of Zinc, treated femurs harvested 4 weeks post-surgery, showing spiral fracture indicative of healing, compared to (C) ZINC 3 (control) showing non-spiral fracture indicative of non-union (Left: Intact Femur, Right: Fractured Femur).

FIG. 7 illustrates 4-week post-fracture radiographs of local manganese chloride ($MnCl_2$) treatment group vs. saline control.

DETAILED DESCRIPTION OF THE INVENTION

Figure 3:
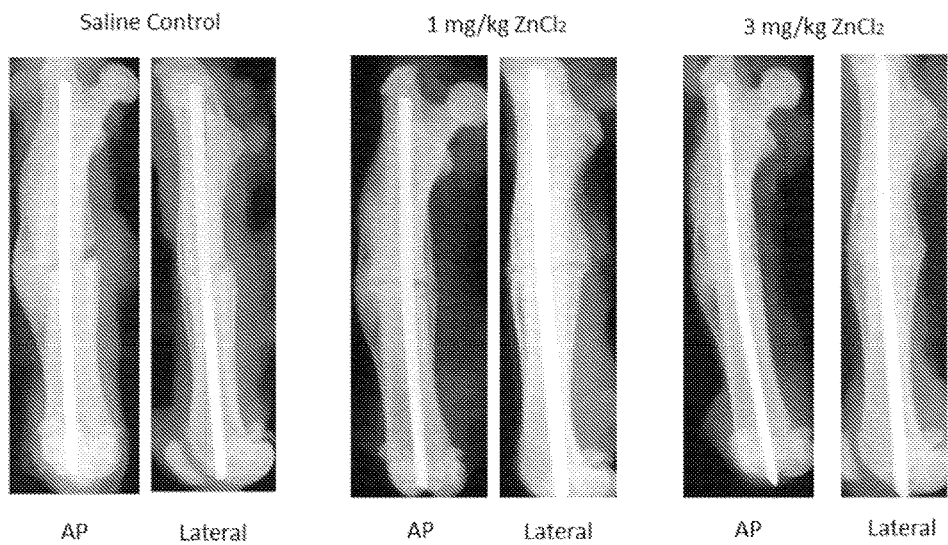
FIG. 3 illustrates 4-week radiographs (AP and Medial-Lateral views) of representative samples of fracture femur bones treated with local $ZnCl_2$ (1.0 and 3.0 mg/Kg) in comparison with saline control.

The present invention is based on the discovery that insulin-mimetics can be used to accelerate bone regeneration by stimulating insulin pathway signaling at a fracture site. In particular, the present invention is based on the discovery that the biological impact of insulin-mimetic agents on bone can be exploited, to play a critical role in bone healing. Insulin-mimetic agents, such as insulin pathway-stimulating zinc, vanadium, tungsten, molybdenum, niobium, selenium, or manganese compounds, delivered locally with or without a carrier, can improve the torsional strength and bone mineral density of regenerated bone. Development of a vanadium, zinc, or similar metal salt therapy to accelerate bone regeneration would be beneficial therapeutically and obviate the need for developing specialized methods to deliver complex molecules, such as protein growth factors like insulin, eliminate specialized storage, enable ease of use, and be cost-effective.

The present invention thus uses an insulin-mimetic agent to treat various hone conditions, such as bone fractures, and to enhance spinal fusion, for example, in treating spinal arthrodesis. The insulin-mimetic agents suitable for the present invention include, but are not limited to, insulin pathway-stimulating zinc, vanadium, tungsten, molybdenum, niobium, selenium, or manganese metal or compounds. For example, we used $ZnCl_2$ alone or as part of a formulation with on orthopedic carrier ($CaSO_4$, for example) and showed accelerated fracture healing when applied directly to the site of fracture post surgery.

Preferably, the patient in need of bone healing is afflicted with a bone condition selected from bone fracture, bone trauma, arthrodesis, including spinal arthrodesis, extremity arthrodesis and the like, and a bone deficit condition associated with post-traumatic bone surgery, post-prosthetic joint surgery, post-plastic bone surgery, post-dental surgery, bone chemotherapy treatment, congenital bone defect, post traumatic bone loss, post surgical bone loss, post infectious bone loss, allograft incorporation or bone radiotherapy treatment.

In another embodiment of this aspect, the bone condition is selected from bone fractures, osseous defects, and delayed unions and non-unions.

Thus, in one aspect, the present invention provides a method of promoting bone healing or regeneration in a patient inflicted with a bone condition, comprising locally administering to said patient a therapeutically effective amount of an insulin pathway-stimulating insulin-mimetic agent.

In one embodiment of this aspect, the insulin-mimetic agent is an insulin pathway-stimulating zinc, vanadium, tungsten, molybdenum, niobium, selenium, or manganese compound.

In another embodiment of this aspect, the insulin-mimetic agent is a zinc, vanadium, or manganese compound.

In another embodiment of this aspect, the insulin-mimetic agent is administered to the bone injury site.

In another embodiment of this aspect, the method of the present invention is used in combination with an allograft method, autograft method, xenograft method, alloplastic graft method, or orthopedic biocomposite method.

In another embodiment of this aspect, the method comprises co-administering a cytotoxic agent, cytokine or growth inhibitory agent with said insulin-mimetic agent.

In another embodiment of this aspect, the method is used in conjunction with an external bone growth stimulator.

In another embodiment of this aspect, the method comprises co-administering a bioactive bone agent with the insulin-mimetic agent.

In another embodiment of this aspect, the bioactive bone agent is selected from the group consisting of peptide growth factors, anti-inflammatory factors, pro-inflammatory factors, inhibitors of apoptosis, MMP inhibitors, and bone catabolic antagonists.

In another embodiment of this aspect, the peptide growth factor is selected from the group consisting of IGF (1,2), PDGF (AA, AB, BB), BMPs, FGF (1-20), TGF-beta (1-3), aFGF, bFGF, EGF, VEGF, parathyroid hormone (PTH), and parathyroid hormone-related protein (PTHrP).

In another embodiment of this aspect, the anti-inflammatory factor is selected from the group consisting of anti-TNFa, soluble TNT receptors, IL1ra, soluble IL1 receptors, IL4, IL-10, and IL-13.

In another embodiment of this aspect, the bone catabolic antagonist is selected from the group consisting of bisphosphonates, osteoprotegerin, and statins.

In another embodiment of this aspect, the patient is a mammalian animal.

In another embodiment of this aspect, the patient is a human.

In another embodiment of this aspect, the patient is a non-diabetic human.

In another aspect, the present invention provides use of an insulin-mimetic agent for manufacture of a medicament for accelerating bone healing or regeneration in a patient in need thereof characterized by local administration of said medicament.

In another aspect, the present invention provides orthopedic and spinal implants with at least one bone-contacting surface incorporating the insulin-mimetic compounds and composition of the present invention. Exemplary orthopedic devices include screws, plates, rods, k-wires, pins, hooks, anchors, intramedullary devices, pedicle screws, pedicle hooks, spinal fusion cages, spinal fusion plates, prostheses, porous metal implants such as trabecular metal implants, and the like. Implants suitable for use with the present invention include metal implants formed from metals such as titanium, alloys thereof, tantalum, alloys thereof, cobalt chrome alloys, steel alloys, such as stainless steel, and the like. Polymer implants may also be used, including implants formed from polyglycolic acid (PGA), poly(lactic-co-glycolic acid) (PLGA), polylactic acid (PLA), polycaprolactone (PCL), polyether ether ketone (PEEK), polyethylene terephthalate (PET), polypropylene (PP), polycarbonates (PC), poly(ortho esters) (POEs), and the like.

The insulin mimetic may be coated on the bone-contacting surface of the implant by conventional means. In the alternative the implant may be formulated and fabricated so that the insulin-mimetic is incorporated into the bone-contacting surface of the implant. Means by which this can be accomplished are readily apparent to those of ordinary skill in the art.

In another aspect, the present invention provides a bone injury treatment kit comprising a therapeutically effective amount of an insulin-mimetic agent formulated for local administration to a patient inflicted with a bone condition in need of healing or bone regeneration. Such its may also include a device for local administration, such as a hypodermic syringe.

In another aspect, the present invention provides a bone tissue material, ceramic bone-grail substitute or mixture thereof for facilitating bone regeneration or bone fusion. Bone tissue material suitable for use in the present invention includes autograft, allograft and xenograft materials.

In one embodiment of this aspect, the bone tissue material contains an insulin-mimetic agent selected from insulin pathway-stimulating zinc, Vanadium, tungsten, molybdenum, niobium, selenium, and manganese compounds.

In another embodiment of this aspect, the bone tissue material contains an insulin-mimetic agent selected from vanadium, manganese, and zinc compounds.

In another embodiment of this aspect, the bone tissue material further contains a pharmaceutically acceptable carrier.

In another embodiment of this aspect, the pharmaceutically acceptable carrier is an inorganic salt.

In another embodiment of this aspect, the pharmaceutically acceptable carrier is an inorganic salt selected from sulfates and phosphates.

In another embodiment of this aspect, the pharmaceutically acceptable carrier is a calcium salt.

In another aspect, the present invention provides a spinal fusion procedure utilizing an insulin mimetic agent for enhancing spinal fusion. In one embodiment, a surgical procedure for stabilizing vertebrae in a spine is provided, including the steps of exposing a portion of each of adjacent vertebrae; and placing supplementary bone tissue material, ceramic bone-graft substitute, or mixture thereof, and an insulin-mimetic agent within an area between the exposed portions of the adjacent vertebrae and in contact with the exposed portions of both vertebrae; wherein the insulin-mimetic agent is provided in an amount effective to increase the rate of fusion of the two vertebrae with the bone tissue material.

In one embodiment of this aspect, the insulin-mimetic agent is a zinc, vanadium, tungsten, molybdenum, niobium, selenium, or manganese compound.

In another embodiment of this aspect, the insulin-mimetic agent is a zinc or vanadium compound.

In another embodiment of this aspect, the insulin-mimetic agent is added to the supplementary bone tissue material and/or ceramic bone-graft substitute to provide a supplementary bone tissue material containing the insulin-mimetic agent.

In another embodiment of this aspect, the insulin-mimetic agent is added separately from the supplementary bone tissue material and/or ceramic bone-graft substitute as a composition further comprising a pharmaceutically acceptable carrier. According to one embodiment, the composition is an insulin-mimetic calcium sulfate pellet.

In another embodiment of this aspect, the method is in combination with transplantation of an autograft bone, allograft bone, xenograft bone, ceramic bone-graft substitute, orthopedic biocomposites, and the like. According to one embodiment, an insulin-mimetic agent is admixed with the autograft, allograft, xenograft ceramic bone-graft substitute, orthopedic biocomposites and the like.

Preferred sites of interest in the patient include sites in need of bone healing and areas adjacent and/or contiguous to these sites. Optionally, the treatment method of the present invention is combined with at least one procedure selected from bone autograft, bone allograft methods, methods using autologous growth factor concentrates, autologous stem cell treatment methods, allogeneic stem cell treatment methods, chemical stimulation methods, electrical stimulation methods, low-intensity pulse ultrasound (LIPUS) methods, internal fixation methods, and external fixation methods, which, in the case of spinal fusion, would stabilize the fused vertebrae or increase the rate at which the two adjacent vertebrae fuse together.

The insulin-mimetic zinc compounds suitable for the present invention include inorganic zinc compounds, such as mineral acid zinc salts. Examples of inorganic zinc compounds include, but are not limited to, zinc chloride, zinc sulfate, zinc phosphate, zinc, carbonate, and zinc nitrate, or combinations thereof.

The insulin-mimetic zinc compounds can also be zinc salts of organic acids. Examples of organic acid zinc salts include, but are not limited to, zinc acetate, zinc formate, zinc propionate, zinc gluconate, bis(maltolato)zinc, zinc acexamate zinc aspartate, bis(maltolato)zinc(II) [Zn(ma)2], bis(2-hydroxypyridine-N-oxido)zinc(II) [Zn(hpo)2], bis(allixinato)Zn(II) [Zn(alx)2], bis(6-methylpicolinato)Zn(II) [Zn(6mpa)2], bis(aspirinato)zinc(II), bis(pyrrole-2-carboxylato)zinc [Zn(pc)2], bis(alpha-furonic acidato)zinc [Zn(fa) 2], bis(thiophene-2-carboxylato)zinc [Zn(tc)2], bis(thiophene-2-acetato)zinc [Zn(ta)2], (N-acetyl-L-cysteinato)Zn (II) [Zn(nac)], zinc(II)/poly(γ-glutamic acid) [Zn(γ-pga)], bis(pyrrolidine-N-dithiocarbamate)zinc(II) [Zn(pdc)$_2$], zinc (II) L-lactate [Zn(lac)$_2$], zinc(II) D-(2)-quinic acid [Zn (qui)$_2$], bis(1,6-dimethyl-3-hydroxy-5-methoxy-2-pentyl-1, 4-dihydropyridine-4-thionato)zinc(II) [Zn(tanm)2], β-alanyl-L-histidinato zinc(II) (AHZ), or the like, or combinations thereof. In another embodiment, the organic acid of zinc salt is a naturally occurring fatty acid.

Suitable organovanadium-based insulin-mimetic agents include, but are not limited to, vanadyl acetylacetonate (VAC), vanadyl sulfate (VS), vanadyl 3-ethylacetylacetonate (VET), and bis(maltolato)oxovanadium (BMOV), and the like. In a preferred embodiment, the organovanadium compound is vanadyl acetylacetonate (VAC). Vanadyl acetylacetonate (VAC), an organic vanadium compound, has demonstrated insulin-mimetic effects in type 1 and type 2 diabetic animals and human studies and prevented some of the associated complications of diabetes in animal studies. Additional pharmacological activities of VAC, which have been studied, include the inhibition of gluconeogenesis, a decrease in glutamate dehydrogenase activity, and antilipolysis. Use of these vanadium-based insulin-mimetic agents to accelerate bone healing or regeneration, or as therapeutic adjuncts for cartilage injury and repair been disclosed by the present inventors in related U.S. Provisional Application Nos. 61/295,234 and 61/504,777; and PCT Application Nos. PCT/US11/21296 and PCT/US12/45771, which are hereby incorporated by reference in their entirety. Insulin-mimetic vanadium compounds suitable for use in the present invention include the compounds disclosed in U.S. Pat. Nos. 5,300,496; 5,527,790; 5,688,784; 5,866,563; 5,888,893; 6,268,357 and 6,287,586, the disclosures of all of which are incorporated herein by reference.

Suitable tungsten, selenium, molybdenum, niobium, or manganese compounds as insulin mimetics for bone healing or regeneration are also encompassed by the present disclosure, and their forms and administration modes are within the grasp of an ordinary skill in the art.

Examples of tungsten compounds include, but are not limited to, sodium tungstate $[Na_2WO_4 \cdot xH_2O]$, tungstophosphoric acid $[H_3[P(W_3O_{10})_4] \cdot xH_2O]$, alanine complex of tungstophosphoric acid (WPA-A) $[H_3[P(W_3O_{10})_4][CH_3CH(NH_2)COOH] \cdot xH_2O]$, homo-polyoxotungstates and vanadium polyoxotungstates, tungsten (VI) perooxo complexes (e.g., $(gu)_2[WO_2(O_2)_2]$ and $(gu)[WO(O_2)_2(quin-2-c)]$, wherein "gu" is guanidinium and "quin-2-c" is quinoline 2-carboxylate), and permetalloxide of tungstate (pW). Molybdenum compounds include, for example, permetalloxide of molybdate.

Niobium compounds include, but are not limited to, Nb(V) peroxo complexes, e.g., $(gu)_3[Nb)(O_2)_4]$ and $(gu)_2[Nb(O_2)_3(quin-2-c)$, wherein "gu" is guanidinium and "quin-2-c" is quinoline 2-carboxylate.

Selenium compounds include, but are not limited to, sodium selenate $[Na_2SeO_4 \cdot xH2O]$ and sodium selenite $[Na_2SeO_3 \cdot xH_2O]$.

Manganese compounds include, but are not limited to, 3-O-methyl-D-chiro-inositol+manganese chloride ($MnCl_2$), D-chiro-inositol+manganese chloride ($MnCl_2$), manganese sulfate [MnSO4], inositol glycan pseudo-disaccharide Mn(2+) chelate containing D-chiro-inositol 2a (as pinitol) and galactosamine, oral manganese, manganese oxides, e.g., $MnO_2$, $MnOAl_2O_3$, and $Mn_3O_4$.

Other insulin-mimetic metal compounds, in particular, vanadium, zinc, manganese, and tungsten compounds, that may be used for the present invention include those disclosed in, for example, Wong. V. V., et al., *Cytotechnology*, 2004, 45(3):107-15; and Nomiva, K., et al., *J. Inorg. Biochem.* 2001, 86(4): 657-667, which are hereby incorporated by reference.

Advantages of small molecules (such as zinc, vanadium, tungsten, molybdenum, niobium, selenium, or manganese) insulin-mimetic agents include, but are not limited to: (a) development of a small molecule insulin mimetic can be of great significance to bone fracture patients; (b) insulin composite which requires a carrier may be difficult to meet FDA requirements as a dual agent product; and (c) small molecule insulin mimetics may have longer half life and avoid the storage issues commonly seen with proteins.

Exemplary healing mechanisms include, but are not limited to: (a) retaining mineralized components in bone, (b) inhibiting release of mineralized components from bone, (c) stimulating osteoblast activity, (d) reducing osteoclast activity, or (e) stimulating bone remodeling.

The term "therapeutically effective amount," as used herein, means an amount at which the administration of an agent is physiologically significant. The administration of an agent is physiologically significant if its presence results in a detectable change in the bone healing process of the patient.

The term "bone injury," "injured bone," or the like, as used herein, refers to a bone condition selected from the group consisting of bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In another embodiment of this aspect, the method is employed in a spinal fusion procedure. Insulin-mimetic compositions of the present invention are particularly useful adjuncts for spinal fusion procedures. The compositions may be used to promote vertebral fusion and spinal stabilization and also to improve function of spinal stabilization devices.

According to one embodiment, an interbody device, which is a prosthetic implant configured to stabilize two adjacent vertebrae and promote fusion of the two vertebrae, is provided, wherein the bone tissue contacting surfaces of the prosthetic implant are the device coated with a composition comprising an insulin-mimetic agent. The device may also be configured to supply autograft bone, allograft bone, xenograft bone, ceramic bone-graft substitutes, orthopedic biocomposites, or the like, to the exposed surfaces of the two adjacent vertebrae, which bone or hone-graft substitute may or may not be admixed with an insulin-mimetic agent.

In another aspect, the present invention provides a bone tissue kit for facilitating fusion of vertebrae in a spinal fusion surgical procedure, including a composition containing an insulin-mimetic agent and a pharmaceutically acceptable carrier. In an embodiment the kit also contains allograft bone tissue material, xenograft bone tissue material, and/or ceramic bone-graft substitute. In one embodiment the insulin-mimetic agent and the allograft bone tissue material, xenograft bone tissue material, and/or ceramic bone-graft substitute are provided in a mixture. In another embodiment, the insulin-mimetic agent and allograft bone tissue material, xenograft bone tissue material, or ceramic bone-graft substitute are provided for subsequent mixing.

In one embodiment of this aspect, the insulin-mimetic agent is selected from insulin pathway-stimulating zinc, vanadium, tungsten, molybdenum, niobium, selenium, and manganese compounds, and combinations thereof. The insulin-mimetic agent can be in any form known in the art that is suitable for use in spinal fusion procedures.

In another aspect, the present invention provides a composition comprising an insulin-mimetic, agent for enhancing spinal fusion in a spinal fusion surgical procedure, wherein the composition contains an insulin-mimetic agent and a pharmaceutically acceptable carrier. In one embodiment, the composition contains allograft bone material and/or ceramic bone-graft substitute.

In one embodiment of this aspect, the insulin-mimetic agent is selected from insulin pathway-stimulating zinc, vanadium, tungsten, molybdenum, niobium, selenium, and manganese compounds, and combinations thereof.

In one embodiment of this aspect, the implantable device is combined with autograft, allograft, or synthetic bone void fillers (e.g. ceramic) in order to enhance posterior or posterolateral fusion of the cervical, thoracic or lumbar spine. This involves decortication of the native host bone of the lamina or lateral masses (posterior fusion) or the side of the facet joints and transverse processes (posterolateral fusion).

The bone grafting mixture (including the insulin-mimetic compound) are then packed over these prepared areas to induce segmental fusion.

In another embodiment of this aspect, the implantable device is combined with autograft, allograft, or synthetic (ceramic) bone void filler in the central chamber of an interbody device to enhance fusion between the vertebral bodies of the anterior column of the spine (anterior interbody spinal fusion). This is performed after anterior discectomies and decompressions as well as after anterior corpectomies when the vertebral body is removed for purposes of decompression or to address trauma, tumor or infection involving the vertebral body.

In another embodiment of this aspect, an insulin-mimetic agent is used as a surface modification to an interbody device (cage) inserted between the vertebral bodies of the anterior column of the spine to effect an anterior interbody spinal fusion. Such cages are used to reconstruct the anterior column of the spine after discectomy or corpectomy (see above). The areas requiring surface modification would be the surfaces that will be in apposition to the corresponding vertebral endplates of the segments cephalad (above) and caudal (below).

In another embodiment of this aspect, an insulin-mimetic agent is used as a surface modification to spinal fixation devices such as pedicle screws, inserted by either open or percutaneous posterior approach. Such screws are placed by drilling a pilot hole that extends down through the pedicle and into the vertebral body in a posterior-to-anterior direction. The screws in each vertebral body are then connected to each other by rods to stabilize the spanned motion segments.

In another embodiment of this aspect, an insulin-mimetic agent is used as a surface modification to spinal fixation devices such as anterior vertebral body screws used in conjunction with plates, inserted by open or minimally invasive anterior or anterolateral approaches. Such anterior vertebral body screws are typically placed in an anterior-to-posterior direction in the cervical and lower lumbar spine. In the upper lumbar and thoracic spine they are often placed into the vertebral body from an anterolateral starting point.

In any of the embodiments of this aspect, the insulin-mimetic agent is selected from zinc, vanadium, tungsten, molybdenum, niobium, selenium, or manganese compounds, and combinations thereof, preferably a vanadium, manganese, or zinc compound, for example, VAC, manganese chloride, or zinc chloride.

Examples of diseases or conditions that make a patient in need of spinal fusion include, but are not limited to, arthrodesis, degenerative disc disease, spinal disc herniation, discogenic pain, spinal tumor, vertebral fracture, scoliosis, kyphosis (i.e., Scheuermann's disease), spondylolisthesis, spondylosis, Posterior Rami Syndrome, other degenerative spinal conditions, and any other conditions that cause instability of the spine.

It will be appreciated that actual preferred amounts of a pharmaceutical composition used in a given therapy will vary depending upon the particular form being utilized, the particular compositions formulated the mode of application, and the particular site of administration, and other such factors that are recognized by those skilled in the art including the attendant physician or veterinarian. Optimal administration rates for as given protocol of administration can be readily determined by those skilled in the art using conventional dosage determination tests.

Dosages of an insulin-mimetic suitable for the present invention may vary depending on the particular use envisioned. The determination of the appropriate dosage or route of administration is well within the skill of an ordinary physician. The dosage regimen for the insulin-mimetic agents of the present invention will vary depending upon known factors, such as the pharmacodynamic characteristics of the particular agent, and its mode and route of administration; the species, age, sex, health, medical condition, and weight of the recipient; the nature and extent of the symptoms; etc. For example, the local dosage of a particular insulin-mimetic agent, such as a zinc, vanadium, or manganese compound, may depend more on the bone condition than on the weight of a patient. A dosage of local administration may significantly differ from a dosage of systemic administration, and a dosage of administration in a solution form may differ from a dosage when it is administered through the surface coating on an implantable device. Without being bound by any particular theory, the dosage of an insulin-mimetic agent according to the present invention should be at a level so that the insulin pathway in a patient is stimulated in order to accelerate the bone healing or regeneration process.

By way of general guidance, the dosage of each active ingredient, when used for the indicated effects, will range between about 0.001 to about 200 mg/Kg based on a patient's weight, preferably between about 0.01 to about 100 mg/Kg, and most preferably between about 0.1 to about 50 mg/Kg. The doses can be repeated whenever needed, or considered to be beneficial to the bone healing and regeneration processes as determined by a physician, for example, once daily, once weekly, once every other week, once monthly, or any other time period that may provide most benefits to a particular patient.

The route of administration of "local zinc" via "insulin mimetic delivery system" is in accordance with known methods, e.g. via immediate-release, controlled-release, sustained-release, and extended-release means. Preferred modes of administration for the insulin-mimetic delivery system include injection directly into afflicted bone or a fusion site and areas adjacent and/or contiguous to these sites, or surgical implantation of insulin-mimetic agent(s) directly into the fusion sites and area adjacent and/or contiguous to these sites. This type of system will allow temporal control of release as well as location of release as stated above.

The formulations used herein may also contain more than one active compound as necessary for the particular indication being treated, preferably those with complement-ary activities that do not adversely affect each other. Alternatively, or in addition, the formulation may comprise a cytotoxic agent, cytokine or growth inhibitory agent. Such molecules are present in combinations and amounts that are effective for the intended purpose.

Vanadium, which exists in +4 (vanadyl) and +5 (vanadate) compounds in the biological body, have demonstrated poor absorption rates within the gastrointestinal (GI) tract and GI side-effects, such as diarrhea and vomiting. As a result, additional organic vanadium compounds, i.e., vanadyl 3-ethylacetylacetonate (VET), bis(maltolato)oxo-vanadium (BMOV), and VAC, have been synthesized in order to improve absorption and safety. VAC with an organic ligand has been proven to be more effective in its anti-diabetic function compared with other vanadium compounds, including BMOV, VS, and VET.

Therapeutic formulations of vanadium compounds in the vanadium delivery systems employable in the methods of the present invention are prepared for storage by mixing the vanadium compound having the desired degree of purity with optional pharmaceutically acceptable carriers, excipients, or stabilizers (Remington's Pharmaceutical Sciences 16th edition, Osol, A. Ed. (1980)). Such therapeutic formulations can be in the form of lyophilized formulations or aqueous solutions. Acceptable biocompatible carriers, excipients, or stabilizers are nontoxic to recipients at the dosages and concentrations employed, and may include buffers, for example, phosphate, citrate, and other organic acids; antioxidants including ascorbic acid and methionine; preservatives (e.g. octadecyldimethylbenzyl ammonium chloride; hexa-methonium chloride; benzalkonium chloride, benzethonium chloride; phenol, butyl or benzyl alcohol; alkyl parabens, for example, methyl or propyl paraben; catechol; resorcinol; cyclohexanol; 3-pentanol; and m-cresol); low molecular weight (less than about 10 residues) polypeptides; proteins, for example, serum albumin, gelatin, or immunoglobulins, hydrophilic polymers, for example, polyvinylpyrrolidone; amino acids, for example, glycine, glutamine asparagine, histidine, arginine, or lysine; monosaccharides, disaccharides, and other carbohydrates including glucose, mannose, dextrins, or hyaluronan; chelating agents, for example, EDTA, sugars, for example, sucrose, mannitol, trehalose or sorbitol; salt-forming counter-ions, for example, sodium; metal complexes (e.g. Zn-protein complexes); and/or non-ionic surfactants, for example, TWEEN™, PLURONICS™ or polyethylene glycol (PEG).

In order for the formulations to be used for in vivo administration, they must be sterile. The formulation may be readily rendered sterile by filtration through sterile filtration membranes, prior to or following lyophilization and reconstitution. The therapeutic formulations herein preferably are placed into a container having a sterile access port, for example, an intravenous solution bag or vial having a stopper pierceable by a hypodermic injection needle.

The vanadium may also be entrapped in microcapsules prepared, for example by coacervation techniques or by interfacial polymerization, for example, hydroxy-methylcellulose or gelatin-microcapsules and poly-(methylmethacrylate) microcapsules, respectively. Such preparations can be administered in colloidal drug delivery systems (for example, liposomes, albumin microspheres, microemulsions, nano-particles and nanocapsules) or in macroemulsions. Such techniques are disclosed in Remington's Pharmaceutical Sciences, 16th Edition (or newer), Osol A. Ed. (1980).

Optionally, the organovanadium agent in the vanadium delivery systems includes a porous calcium phosphate, non-porous calcium phosphate, hydroxy-apatite, tricalcium phosphate, tetracalcium phosphate, calcium sulfate, calcium minerals obtained from natural bone, inorganic bone, organic bone, or a combination thereof.

Where sustained-release or extended-release administration of vanadium in the vanadium delivery systems is desired, microencapsulation is contemplated. Microencapsulation of recombinant proteins for sustained release has been successfully performed with human growth hormone (rhGH, interferon-α, -β, -γ (rhIFN-α,-β,-γ), interleukin-2, and MN rgp120. Johnson et al., Nat. Med. 2: 795-799 (1996): Yasuda, Biomed. Ther. 27: 1221-1223 (1993): Hora et al., Bio/Technology 8: 755-758 (1990); Cleland, "Design and Production of Single Immunization Vaccines Using Polylactide Polyglycolide Microsphere Systems" in Vaccine Design: The Subunit and Adjuvant Approach, Powell and Newman, eds., (Plenum Press: New York, 1995), pp. 439-462: WO 97/03692, WO 9640072, WO 96/07399 and U.S. Pat. No. 5,654,010.

Suitable examples of sustained-release preparations include semipermeable matrices of solid hydrophobic polymers containing the vanadium in the vanadium delivery systems, which matrices are in the form of shaped articles, e.g. films, or microcapsules. Examples of sustained-release matrices include one or more polyanhydrides (e.g., U.S. Pat. Nos. 4,891,225; 4,767,628), polyesters, for example, polyglycolides, polylactides and polylactide-co-glycolides (e.g., U.S. Pat. No. 3,773,919; U.S. Pat. No. 4,767,628; U.S. Pat. No. 4,530,840; Kulkarni et al., Arch. Surg. 93: 839 (1966)), polyamino acids, for example, polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly(vinyl-alcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and .gamma.-ethyl-L-glutamate, non-degradable ethylene-vinyl acetate, degradable lactic acid-glycolic acid copolymers, for example, the LUPRON DEPOT™ (injectable microspheres composed of lactic acid-glycolic acid copolymer and leu-prolide acetate), and poly-D-(−)-3-hydroxybutyric acid. While polymers such as ethylene-vinyl acetate and lactic acid-glycolic acid enable release for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate but rate and cellulose acetate propionate.

Alternatively, sustained-release formulations may be composed of degradable biological materials, for example, collagen and derivatives thereof, bioerodible fatty acids (e.g., palimitic acid, steric acid, oleic acid, and the like). Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957,744: Valle et al., Polym. Mater. Sci. Eng., 62: 731-735 (1991). HA polymer grafted with polyethylene glycol has also been prepared as an improved delivery matrix which reduced both undesired drug leakage and the denaturing associated with long term storage at physiological conditions. Kazuteru, M., J. Controlled Release 59:77-86 (1999). Additional biodegradable polymers which may be used are poly(caprolactone), polyanhydrides, polyamino acids, polyorthoesters, polycyanoacrylates, poly(phosphazines), poly(phosphodiesters), poly-esteramides, polydioxanones, polyacetals, polyketals, polycarbonates, polyorthocarbonates degradable and nontoxic polyurethanes, polyhydroxylbutyrates, polyhydroxy-valerates, polyalkylene oxalates, polyalkylene succinates, poly(malic acid), chitin, and chitosan.

Alternatively, biodegradable hydrogels may be used as controlled-release materials for the vanadium compounds in the vanadium delivery systems. Through the appropriate choice of macromers, membranes can be produced with a range of permeability, pore sizes and degradation rates suitable for different types of vanadium compounds in the vanadium delivery systems.

Alternatively sustained-release delivery systems for vanadium in the vanadium delivery systems can be composed of dispersions. Dispersions may further be classified as either suspensions or emulsions. In the context of delivery vehicles for a vanadium compound, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also blown as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with a vanadium compound in the present invention include multiple emulsions, microemulsions, microdroplets and liposomes. Micro-droplets are unilamellar phospholipid vesicles that consist of a spherical lipid layer with an oil phase inside. E.g., U.S. Pat. No. 4,622,219 and U.S. Pat. No. 4,725,442. Liposomes are phospholipid vesicles prepared by mixing water-insoluble polar lipids with an aqueous solution.

Alternatively, the sustained-release formulations of vanadium in the vanadium delivery systems may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in Biodegradable Polymers as Drug Delivery Systems M. Chasin and R. Langeer, editors (Marcel Dekker: New York, 1990), pp. 1-41.

As an illustrated example, an insulin-mimetic may be continuously administered locally to a site via a delivery pump. In one embodiment, the pump is worn externally (in a pocket or on the belt) and attached to the body with a long, thin, and flexible plastic tubing that has a needle or soft cannula (thin plastic tube), and the cannula or needle is inserted and then left in place beneath the skin. The needle or cannula and tubing can be changed, for example, every 48 to 72 hours. The pump would store the insulin-mimetic in a cartridge and release it based on the optimal delivery rate. Optionally, the pump is programmed to give a small dose of a drug continuously through the day and night, which in certain circumstances may be preferred.

Various applications of the present invention are listed in Table 1.

TABLE 1

Applications of local administration of insulin-mimetics.

| Application | Method | Examples |
| --- | --- | --- |
| Fracture Healing | Local delivery to closed or open fractures | Bone fractures treated by closed reduction or surgical reduction |
| Fracture Non-unions | Local delivery to non-healing fractures | Treatment of fractures that have experienced delayed or failed healing |
| Arthrodesis/fusion (e.g., spine, fusion of joints such as foot and ankles, wrist) | Injection to increase osteogenesis in certain joints | Treatment of spine fusion |
| Allograft incorporation | Injection within and around allograft used to fill defect | Treatment of intercalary defect after traumatic injuries, tumor resection, failed arthroplasty, etc. |

The compounds and compositions of the present invention are effective insulin mimetics without the issues associated with biologics such as insulin. They have various notable advantages over biologics, for example, their high tolerance to manufacturing process and conditions (e.g., elevated temperatures). In the case of $ZnCl_2$ it is a known, highly stable compound commonly used in medical products, has a long shelf life, and has no storage and contamination/sterilization related issues.

The compounds and compositions of the present invention are also versatile—they can be used directly or as part of a formulation with a carrier applied to the site of fracture to accelerate fracture healing. No special techniques need to be developed in order to use the inventions described. For example, zinc compounds can be applied directly to the fracture site as part of the surgery or intramedullary.

Similarly, vanadium-based insulin mimetics can accelerate fracture healing process (fracture healing resolved in 4-5 weeks), reduced time to recovery in both normal and diabetic patients), resolve non-healing fractures (10% of annual total), resolve diabetic (compromised host model) fractures, in addition to a wide array of applications in several sectors of orthopedic devices. In the case of the vanadium surface modification approach, vanadium can be used to modify existing implants (plates, nails, screws, k-wires, etc.) to potentiate osseous healing.

Similar to the zinc compounds, vanadium compounds are also effective insulin mimetics without the issues associated with biologics such as insulin. They have the following advantages over biologics, for example, the ability to tolerate manufacturing process (for example, elevated temperatures), the high stability and long shelf life, and no storage and contamination/sterilization issues. Moreover, the disclosed vanadium compounds are versatile—they can be used directly or as part of a formulation with a carrier applied to the site of fracture to accelerate fracture healing. Surfaces of materials commonly used in orthopedic implants can be modified with vanadium and such modified materials were also shown to be effective in accelerating fracture healing. No special techniques need to be developed in order to use the inventions described. In the case of vanadium compounds, the material can be applied directly to the fracture site as part of the surgery or percutaneously injected. In the case of the surface modified implants, standard surgical techniques associated with the implants can be used. In the present studies disclosed, the quality of the bone formation was characterized using X-ray, micro-CT scans as well as measuring mechanical parameters such as torque, rigidity, shear modulus and shear stress, and in all cases, the quality of the healed bone was compared to that of normal bone in the same animal.

When an implantable device coated by a composite surface coating comprising an insulin-mimetic compound of the present invention is used, the coating can be formed by any methods known in the relevant art, for example, without limitation, those disclosed in Petrova. R. and Suwattananont, N., *J. Electr. Mat.*, 34(5):8 (2005)). For example, suitable methods include chemical vapor deposition (CVD), physical vapor deposition (PVD), thermochemical treatment, oxidation, and plasma spraying (Fischer, R. C., *Met. Progr.* (1986); Habig, K. H., *Tribol. Int.*, 22:65 (1989)). A suitable coating of the present invention may also comprise combinations of multiple, preferably two or three, layers obtained by forming first boron diffusion coating followed by CVD (Z. Zakhariev, Z., et al. *Surf Coating Technol.*, 31:265 (1987)). Thermochemical treatment techniques have been well investigated and used widely in the industry. This is a method by which nonmetals or metals are penetrated by thermodiffusion followed by chemical reaction into the surface. By thermochemical treatment, the surface layer changes its composition, structure, and properties.

Other suitable coating techniques may include, but are not limited to, carburizing, nitriding, carbonitriding, chromizing, and aluminizing. Among these coating techniques, boronizing, being a thermochemical process, is used to produce hard and wear-resistant surfaces. As a person of ordinary skill in the art would understand, different coating techniques may be used to make the vanadium-based coatings and coated devices of the present invention in order to have desired properties suitable for specific purposes.

The present invention also finds wide application in veterinary medicines to treat a variety of factures or enhance spinal fusion in a mammalian animal, including but not limited to, horses, dogs, cats, or any other domestic or wild mammalian animals. A particular useful application may be found, for example, in treating an injured racehorse.

The following non-limiting examples illustrate certain aspects of the invention.

EXAMPLES

Example 1

Use of Zinc Compounds to Accelerate Bone Fracture Healing

Materials and Methods
The BB Wistar Rat Model
Animal Source and Origin

Diabetic Resistance (DR) BB Wistar rats used in the study were obtained from a breeding colony at UMDNJ-New Jersey Medical School (NJMS). The rats were housed under controlled environmental conditions and fed ad libitum. All research protocols were approved by the Institutional Animal Care and Use Committee at University of Medicine and Dentistry of New Jersey-New Jersey Medical School.
Diabetic Resistant BB Wistar Rats A total of 24 DR BB Wistar rats were utilized in the study. Due to unstable fixation during mechanical testing, three samples were removed. Another sample was removed due to complications associated with a post-operative infection. The remaining 17 animals were used for mechanical testing and were distributed between the control saline (n=6), 0.1 mg/kg zinc chloride (n=2), 1.0 mg/kg zinc chloride (n=3), 3.0 mg/kg zinc chloride (n=3), 6.0 mg/kg zinc chloride (n=4) and 10.0 mg/kg zinc chloride (n=3) groups.
Closed Femoral Fracture Model Surgery was performed in DR animals between ages 93 and 99 days using a closed mid-diaphyseal fracture model, on the right femur as described previously.

General anesthesia was administrated by intraperitoneal (IP) injection of ketamine (60 mg/kg) and xylazine (8 mg/kg). The right leg of each rat was shaved and the incision site was cleansed with Betadine and 70% alcohol. An approximately 1 cm medial, parapatellar skin incision was made over the patella. The patella was dislocated laterally and the interchondylar notch of the distal femur was exposed. An entry hole was made with an 18 gauge needle and the femur was reamed with the 18 gauge needle. A Kirschner wire (316LVM stainless steel, 0.04 inch diameter. Small Parts, Inc., Miami Lakes, Fl.) was inserted the length of the medullary canal, and drilled through the trochanter of the femur. The kirschner wire was cut flush with the femoral condyles. After irrigation, the wound was closed with 4-0 vicryl resorbable suture. A closed midshaft fracture was then created unilaterally with the use of a three-point bending fracture machine. X-rays were taken to determine whether the fracture was of acceptable configuration. An appropriate fracture is an approximately mid-diaphyseal, low energy, transverse fracture (FIG. 1). The rats were allowed to ambulate freely immediately post-fracture. This closed fracture model is commonly used to evaluate the efficacy of osseous wound healing devices and drugs.
Local Zinc Delivery Zinc Chloride [($ZnCl_2$) Sigma Aldrich, St. Louis, Mo.] mixed with a buffer was injected into the intramedullary canal prior to fracture. The buffer consisted of sodium acetate, sodium chloride methyl hydroxybenzoate, and zinc chloride. Doses of 1.0 mg/kg and 3.0 mg/kg zinc chloride were tested and administered at a volume of 0.1 mL.
Mechanical Testing Fractured and contralateral femora were resected at three and four weeks post-fracture. Femora were cleaned of soft tissue and the intramedullary rod was removed. Samples were wrapped in saline (0.9% NaCl) soaked gauze and stored at −20° C. Prior to testing, all femora were removed from the freezer and allowed to thaw to room temperature for three to four hours. The proximal and distal ends of the fractured and contralateral femora were embedded in ¾ inch square nuts with Field's Metal, leaving an approximate gauge length of 18 mm (FIG. 2). After measuring callus, gauge length and femur dimensions, torsional testing was conducted using a servohydraulics machine (MTS Systems Corp., Eden Prairie, Minn.) with a 20 Nmm reaction torque cell (Interface, Scottsdale, Ariz.) and tested to failure at a rate of 2.0 deg/sec. The maximum torque to failure and angle to failure were determined from the force to angular displacement data.

Maximum torque to failure, maximum torsional rigidity, shear modulus, and maximum shear stress were calculated through standard equations (Ekeland, A. et al., *Acta Orthop. Sand.*, 1981, 52(6):605-13: Engesaeter, L. B. et al., *Acta Orthop. Scand.*, 1978, 49(6):512-8). Maximum torque to failure and maximum torsional rigidity are considered extrinsic properties while shear modulus and maximum shear stress are considered intrinsic properties. Maximum torque to failure was defined as the point where an increase in angular displacement failed to produce any further increase in torque. Maximum torsional rigidity is a function of the maximum torque to failure, gauge length (distance of the exposed femur between the embedded proximal and distal end) and angular displacement. Maximum shear stress is a function of the maximum torque to failure, maximum radius within the mid-diaphyseal region and the polar moment of inertia. The polar moment of inertia was calculated by modeling the femur as a hollow ellipse. Engesaeter et al. (1978) demonstrated that the calculated polar moment of inertia using the hollow ellipse model differed from the measured polar moment of inertia by only two percent (Engesaeter, L. B., et al., *Acta Orthop, Scand.*, 1978, 49(6): 512-8).

In order to compare the biomechanical parameters between different treatment groups, the data was normalized by dividing each fractured femur value by its corresponding intact, contralateral femur value (FIG. 2). Normalization was used to minimize biological variability due to differences in age and weight among rats.

In addition to the biomechanical parameters determined through torsional testing, the mode of failure can also provide substantial information. The mode of torsional failure as determined by gross inspection provided an indication as to the extent of healing. A spiral failure in the mid-diaphyseal region indicated a complete union while a transverse failure through the fracture site indicated a nonunion. A combination spiral/transverse failure indicated a partial union (FIG. 2).

Data and Statistical Analysis

Analysis of variance (ANOVA) was performed followed by Holm-Sidak post-hoc tests to determine differences between the treated $ZnCl_2$ groups with a group size larger than two. A Student's t-test was performed to identify differences between the two treated groups in the $ZnCl_2$ study (SigmaStat 3.0, SPSS Inc., Chicago, Ill.). A P value less than 0.05 was considered statistically significant.

General Description of Animal Surgery

A closed mid-diaphyseal fracture surgery was performed on the right femur of each rat as described previously. (Beam. H. A., et al., *J. Orthop. Res.* 2002, 20(6):1210-1216, Gandhi, A., et al., *Bone* 2006, 38(4)540-546.) General anesthesia was administered by intraperitoneal injection of ketamine (60 mg/kg) and xylazine (8 mg/kg). A closed, midshaft fracture was then created using a three-point bending fracture instrument (BBC Specialty Automotive, Linden N.J.) and confirmed with X-rays immediately post-fracture.

Preparation of $ZnCl_2$ Solution

Zinc chloride ($ZnCl_2$), Sigma Aldrich, St. Louis, Mo., mixed with sterile water at various doses with or without a calcium sulfate carrier, were injected into the intramedullary canal prior to fracture. Doses of $ZnCl_2$ were not based on each animal's body weight, but on a lower theoretically tolerable dose for a 290-gram BB Wistar rat, which would not elicit heavy metal poisoning or behavioral changes. This weight is over 50 grams lower than the average weight of non-diabetic BB Wistar rats at an age of approximately 90 days (the age of investigation in this study). A 0.1 ml volume of the $ZnCl_2$ solution was administered locally via a single injection into the marrow space for each dose examined.

Preparation of $ZnCl_2/CaSO_4$ Formulation

To prepare the $ZnCl_2/CaSO_4$ mixture, $CaSO_4$ (2 g) were placed in glass vials. The vials were placed in an autoclave and sterilized at for two hours in a dry cycle. $CaSO_4$ powder (0.8 g) was mixed with 400 µl of saline or 400 µl of $ZnCl_2$ solution (1.0 mg/kg) for one minute at room temperature. The mixture was packed into the barrel of a 1 cc sterile syringe and pushed down into the open orifice of the syringe barrel by insertion of the syringe plunger. After attaching an 18-gauge sterile needle to the syringe barrel, 0.1 ml volume of the mixture was directly injected into the rat femoral canal (non-diabetic BB Wistar rat) prior to Kirschner wire insertion and fracture.

Microradiographic Evaluation

Serial microradiographs were obtained from all animals every two weeks after surgery. Under the same anesthesia as described above, the rats were positioned prone and lateral and anteroposterior (AP) radiographs of their femurs were obtained. Radiographs were taken using a Packard Faxitron (MX 20—Radiographic Inspection System) and Kodak MinR-2000 mammography film. Exposures were for 30 seconds at 55 kVp. Magnified radiographs were obtained of resected femurs. Qualitative analysis was performed on all radiographic sample at four weeks post-fracture. Two independent observers individually scored radiographs based on bridging of the lateral and AP femoral orientations. Treatment group averages were computed to estimate healing at 4 weeks post-fracture. The analysis was conducted in a blinded fashion using a validated, five-point radiographic scoring system, 0=no evident bony bridging, 1=bony bridging of one cortex, 2=bony bridging of two cortices, 3=bony bridging of three cortices, and 4=bony bridging of all four cortices. (See Bergenstock, M. W., et al., *J. Orthop. Trauma* 2005, 19(10):717-723.)

Torsional Mechanical Testing

Torsional testing was conducted at four weeks using a servohydraulics machine (MTS Sys. Corp., Eden Prairie, Minn.) with a 20 Nm reaction torque cell (Interface, Scottsdale, Ariz.). Femurs were tested to failure at a rate of 2.0 deg/sec at four and six week time points. The peak torque, torsional rigidity, effective bulk modulus, and the effective maximum shear stress ($\sigma$) were determined with standard equations that model each femur as a hollow ellipse. (Ekeland A., et al., *Acta Orthop. Scand.* 1981, 52(6):605-613; Engesaeter, L. B., al., *Acta Orthop. Scand.* 1978, 49(512-518). In order to compare the biomechanical parameters between different groups, the data was normalized by dividing each fractured femur value by its corresponding intact, contralateral femur value. Torsional mechanical testing is limited by differences in gauge length during bone potting in Field's metal. Placement and dimension of fracture gap can contribute to standard deviations. Finally, this test is limited because it relies on a mathematical model that assumes the femur is a hollow ellipse, as opposed to the natural architecture of femoral bone. (Levenston, M. E. et al., *J. Bone Miner. Res.* 1994, 9(9):1459-1465.)

Early-Stage Healing Analysis by Histomorphometry

The fractured femora were resected at seven days post-fracture, decalcified, dehydrated, embedded in paraffin, and sectioned using standard histological techniques. Sections were stained with Masson's Trichrome (Accustain™ Trichrome Staining kit, Sigma Diagnostics, St. Louis, Mo.) for histological observation using an Olympus BH2-RFCA microscope (Olympus Optical Co., Ltd., Shinjuku-ku, Tokyo, Japan). Digital images were collected using a Nikon DXM1200F digital camera (Nikon, Tokyo, Japan). Cartilage, new bone, and total callus area were measured from the digital images using Image-Pro Plus software (version 5, Media Cybernetics, Inc., Silver Spring, Md.). Total cartilage and new bone area were normalized to total callus area and expressed as the percent area. Two independent reviewers were used to minimize inconsistencies.

Late-Stage Healing Analysis by Histomorphometry

To examine the effects of VAC at later stages of fracture healing, femora were resected from animals in the groups described above at day 21, embedded and sectioned using standard histological techniques. This includes dehydration, soaking in Xylenes, and finally pre-embedding in a layer of Polymethylmethacrylate (PMMA). After embedding in pure PMMA and allowed to solidify in a hot water bath, slides were sectioned from the PMMA blocks, polished, and stained with a combination of Stevenel's blue and Van Gieson picro-fuchsin (SVG). Histological images of fracture calluses were obtained using an Olympus SZX12 upright microscope (Olympus Optical Co, LTD, Japan) connected via a CCD camera (Optronics, Goleta, Calif.) to a personal computer and analyzed with the Bioquant software package (Biometrics, Inc, Nashville, Tenn.). Parameters that were compared include a) callus area, b) percent calcified tissue area, and c) percent cartilage area. Limitations of this procedure include production of slides with high thicknesses, due to the difficulties associated with sectioning PMMA. This limits the number of possible sections that may be cut for staining in addition to analysis of cellular morphology, due to overlapping layers of cells.

General Health of Animals

The age of the BB Wistar rats at the time of fracture surgery varied between 75 and 137 days. However, animals amongst treatment groups were age and sex matched for each experiment. The percent weight change following surgery to the day of sacrifice was similar amongst treatment groups.

Results

General Health

In this experiment, the rats were 93-117 days old at time of fracture. No significant difference in percent weight gain was found between treatment groups from time of fracture until euthanization (Table 2). Blood glucose levels were higher in the zinc chloride treated rats, but the blood glucose values were within the normal range for all treatment groups (Table 2).

TABLE 2

General health of non-DM BB Wistar rats: local zinc ($ZnCl_2$) delivery without a carrier (Mechanical Testing)

| | Blood Glucose (mg/dl) 12 Hours Post-Surgery | % Weight gain |
|---|---|---|
| Saline Control (n = 6) | 81.7 ± 4.3 [a] | 3.5 ± 2.3 |
| 0.1 mg/kg $ZnCl_2$ (n = 2) | 87.0 ± 7.1 [a] | 15.3 ± 11.5 |
| 1.0 mg/kg $ZnCl_2$ (n = 3) | 99.3 ± 3.1 [b] | 11.0 ± 9.4 |
| 3.0 mg/kg $ZnCl_2$ (n = 3) | 105.0 ± 4.4 [b] | 6.9 ± 11.7 |
| 6.0 mg/kg $ZnCl_2$ (n = 4) | 88.0 ± 4.3 [a] | 4.6 ± 2.3 |
| 10.0 mg/kg $ZnCl_2$ (n = 3) | 87.7 ± 8.5 [a] | 4.2 ± 2.0 |

The data represents average values ± standard deviation
[a] represents values significantly less than the 3.0 mg/kg $ZnCl_2$ group; $p < 0.05$
[b] represents values significantly less than the saline group; $p < 0.05$ Microradiographic Evaluation At four weeks post-fracture, femurs from rats treated with $ZnCl_2$ had significantly higher radiograph scores than control femurs (Table 3).

Mechanical Testing Results

Local $ZnCl_2$ (No Carrier)

The effect of local zinc therapy on healing of femur fractures was measured by torsional mechanical testing. At four weeks post-fracture, rats treated with local $ZnCl_2$ displayed improved mechanical properties of the fractured femora compared to the untreated group. Radiographs taken at 4 weeks post-fracture support this finding (FIG. 3). Table 3 represents the radiograph scoring values at two different dosages.

TABLE 3

Radiographic scoring evaluation

| | 4 Weeks Post-Fracture (# of cortices bridged) |
|---|---|
| Saline Control (n = 6) | 1.2 ± 0.75 (n = 6) |

TABLE 3-continued

Radiographic scoring evaluation

| | 4 Weeks Post-Fracture (# of cortices bridged) |
|---|---|
| 1.0 mg/kg $ZnCl_2$ (n = 3) | 3.0 ± 0.6* (n = 3) |
| 3.0 mg/kg $ZnCl_2$ (n = 3) | 3.3 ± 0.6* (n = 3) |

The data represents average values ± standard deviation
*Represent values statistically higher than control, $p < 0.05$ Table 4 summarizes the results of the mechanical testing of the bone for fractured bone, following four weeks of healing. The effective shear stress was 1.6× and 2.2× higher at four weeks post-fracture for the healing femurs from the $ZnCl_2$-treated animals, at dosages of 1.0 mg/kg and 3.0 mg/kg respectively. When normalized to their intact, contralateral femurs, the percent maximum torque to failure, percent torsional rigidity, and percent effective shear modulus, of the fractured femora were 2.0×, 3.8×, and 8.0× higher, respectively, at the dosage of 3 mg/kg $ZnCl_2$ compared to the control group ($p < 0.05$).

The effect of local zinc therapy on healing of femur fractures in normal (non-diabetic) rats was measured by torsional mechanical testing. At 4 weeks post-fracture, fractured femurs from the rats treated with zinc chloride had greater mechanical properties than the fractured femurs from the control group. For the 10 mg/kg $ZnCl_2$ group, the maximum torsional rigidity was significantly greater than the untreated group (Table 4). When the mechanical parameters of the fractured femora were normalized to the intact, contralateral femora, percent maximum torque to failure (saline group vs. 3 mg/kg $ZnCl_2$ group $p < 0.05$), torsional rigidity (saline group vs. 3 mg/kg $ZnCl_2$ group $p < 0.05$), and shear modulus (Saline group vs. 3 mg/kg $ZnCL_2$ group $p < 0.05$, Saline group vs. 10 mg/kg $ZnCL_2$ group $p < 0.05$) were significantly greater in the local zinc treated groups when compared to the saline group (Table 4).

Healing was assessed by radiographic examination and quantified by mechanical testing. Local $ZnCl_2$ treatment improved radiographic appearance and significantly increased the mechanical strength of fractured femurs. At four weeks post-fracture, the average percent maximum torque to failure of the fractured femora for 3.0 mg/kg $ZnCl_2$ was significantly (2.04 times) greater (82.0% of contralateral vs. 27.0%), compared to the untreated saline group. Percent maximum torsional rigidity values for 3.0 mg/kg $ZnCl_2$ was significantly (3.85 times) greater (97.0% of contralateral vs. 20.0%), compared to the untreated saline group. Percent shear modulus values for both low (3.0 mg/kg $ZnCl_2$) and high (10.0 mg/kg $ZnCl_2$) doses were significantly greater, with high dose 8.8 times greater (36.0% of contralateral vs. 4.0%), and low dose 9.0 times greater (39.0% of contralateral vs. 4.0%) compared to the untreated saline group. The data indicate that local $ZnCl_2$ treatment enhanced bone regeneration during fracture healing and indicates that zinc and potentially similar metals can be used as therapeutically as osteogenic drugs.

TABLE 4

Four weeks post-fracture mechanical testing with local zinc (ZnCl$_2$)

Fractured Femur Values

| | Maximum Torque to Failure (Nmm) | Maximum Torsional Rigidity (Nmm$^2$/rad) | Effective Shear Modulus (MPa) | Effective Shear Stress (MPa) |
|---|---|---|---|---|
| Saline Control (n = 6) | 161 ± 48 | 9.9 × 10$^3$ ± 4.7 × 10$^3$ | 2.6 × 10$^2$ ± 1.1 × 10$^2$ | 17 ± 4 |
| 0.1 mg/kg ZnCl$_2$ (n = 2) | 252 ± 13 | 2.1 × 10$^4$ ± 4.2 × 10$^3$ | 1.7 × 10$^3$ ± 3.3 × 10$^2$ | 61 ± 14 |
| 1.0 mg/kg ZnCl$_2$ (n = 3) | 281 ± 86 | 2.2 × 10$^4$ ± 2.7 × 10$^3$ | 9.7 × 10$^2$ ± 3.6 × 10$^2$ | 44 ± 15 |
| 3.0 mg/kg ZnCl$_2$ (n = 3) | 369 ± 74 | 3.1 × 10$^4$ ± 1.1 × 10$^4$ | 1.3 × 10$^3$ ± 6.4 × 10$^2$ | 55 ± 21* |
| 6.0 mg/kg ZnCl$_2$ (n = 4) | 276 ± 190 | 2.9 × 10$^4$ ± 1.6 × 10$^4$ | 1.1 × 10$^3$ ± 7.5 × 10$^2$ | 32 ± 25* |
| 10.0 mg/kg ZnCl$_2$ (n = 3) | 254 ± 36 | 3.6 × 10$^4$ ± 2.5 × 10$^4$ | 3.0 × 10$^3$ ± 1.9 × 10$^{3*}$ | 62 ± 30 |

Fractured Femur Values Normalized to the Contralateral (Intact) Femur

| | Percent Maximum Torque to Failure | Percent Maximum Torsional Rigidity | Percent Effective Shear Modulus | Percent Effective Shear Stress |
|---|---|---|---|---|
| Saline Control (n = 6) | 27 ± 18 | 20 ± 10 | 4 ± 2 | 10 ± 5 |
| 0.1 mg/kg ZnCl$_2$ (n = 2) | 57 ± 12 | 87 ± 14 | 34 ± 4 | 33 ± 14 |
| 1.0 mg/kg ZnCl$_2$ (n = 3) | 65 ± 29 | 55 ± 14 | 32 ± 15 | 18 ± 8 |
| 3.0 mg/kg ZnCl$_2$ (n = 3) | 82 ± 25* | 97 ± 55* | 36 ± 10* | 27 ± 17 |
| 6.0 mg/kg ZnCl$_2$ (n = 4) | 38 ± 20 | 62 ± 35 | 18 ± 12 | 15 ± 10 |
| 10.0 mg/kg ZnCl$_2$ (n = 3) | 41 ± 8 | 73 ± 44 | 39 ± 23* | 27 ± 11 |

Figure 4:
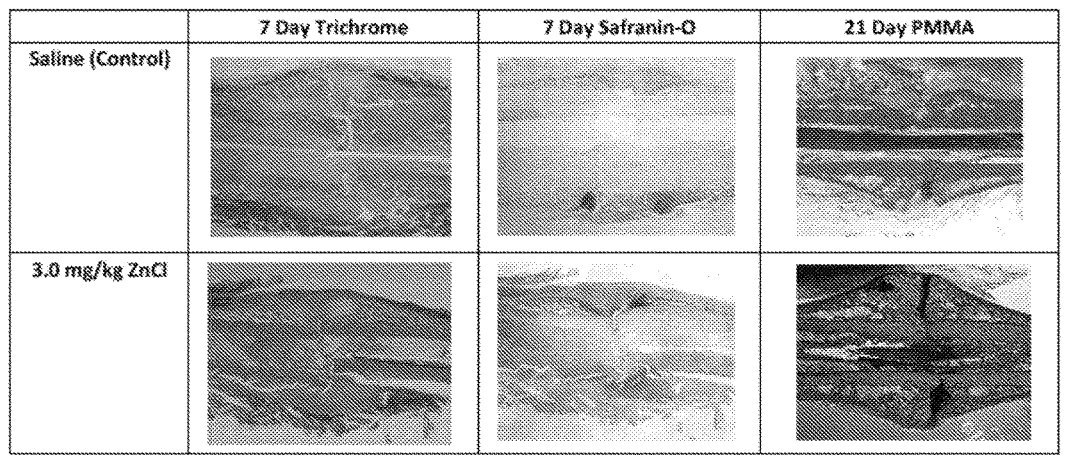
FIG. 4 illustrates histomorphometry of $ZnCl_2$ treated fractures in comparison with saline control.

The data represents average values ± standard deviation
*Represents values statistically higher than saline control, p < 0.05 versus saline control.
One way ANOVA between 6 groups (all pairwise) with a Holm-Sidak post-hoc analysis Histomorphometry of Zinc Chloride Treated Fractures The results of histomorphometry of zinc chloride treated fractures after 7, 10, and 21 days are listed in Table 5 and illustrated in FIG. 4.

TABLE 5

Histomorphometry of zinc chloride-treated fractures

| | % Bone | % Cartilage |
|---|---|---|
| 7 Day | | |
| Saline Control (n = 5) | 8.08 ± 2.45 | 3.00 ± 1.7 |
| 3.0 mg/kg (n = 7) | 18.92 ± 5.97 * | 4.64 ± 3.41 |
| 10 Day | | |
| Saline Control (n = 5) | 17.90 ± 5.20 | 16.3 ± 2.8 |
| 3.0 mg/kg (n = 7) | 21.31 ± 5.40 | 12.79 ± 3.02 |
| 21 Day | | |
| Saline Control (n = 6) | 25.00 ± 6.10 | 6.1 ± 3.2 |
| 3.0 mg/kg (n = 7) | 24.47 ± 3.53 | 11.57 ± 5.53 |

Local ZnCl$_2$/CaSO$_4$ Formulations

Figure 5:
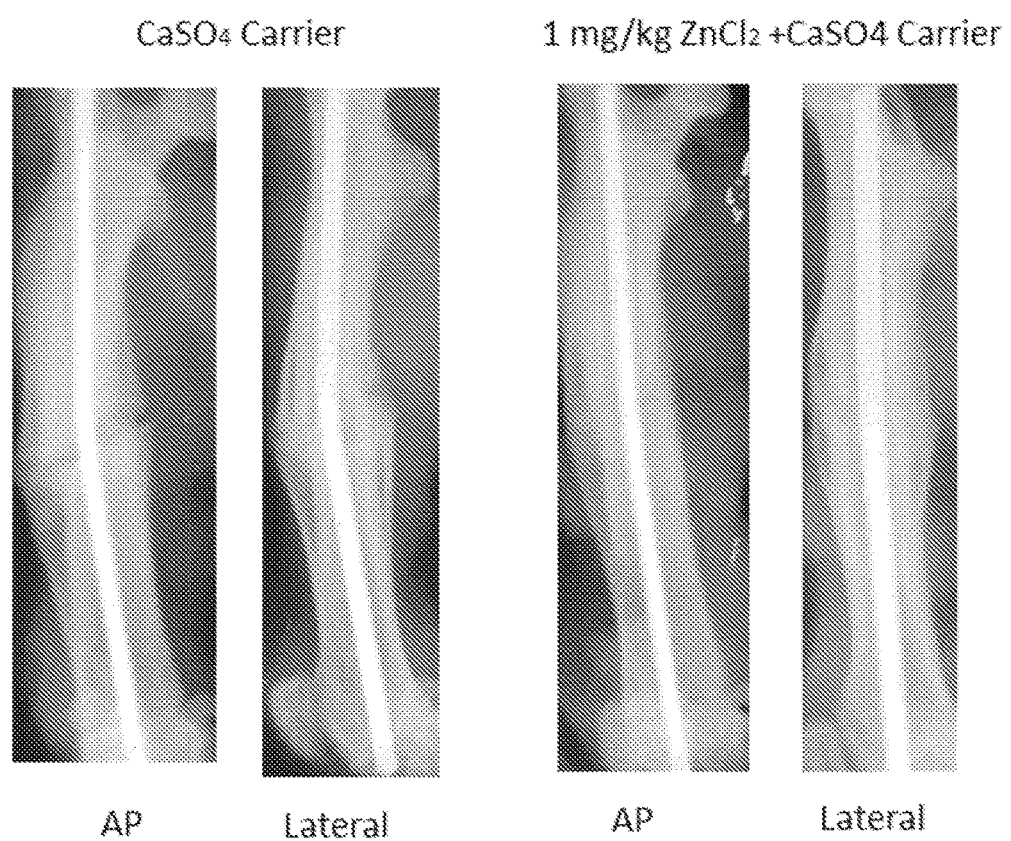
FIG. 5 illustrates 4-week radiographs (AP and Medial-Lateral views) of representative sample for each group of fractured femur bones treated with 1.0 mg/Kg $ZnCl_2$+ $CaSO_4$ carrier in comparison with $CaSO_4$ control.

We repeated the above experiment with formulations of ZnCl$_2$/CaSO$_4$ applied to the fracture site. Radiographs taken at four weeks post-fracture support this finding (FIG. 5) shows significant bone formation.

TABLE 6

Four weeks post-fracture mechanical testing with formulation of zinc chloride (ZnCl$_2$) with CaSO$_4$ carrier applied to the fracture site.

Fractured Femur Values

| | Maximum Torque to Failure (Nmm) | Maximum Torsional Rigidity (Nmm$^2$/rad) | Effective Shear Modulus (MPa) | Effective Shear Stress (MPa) |
|---|---|---|---|---|
| Saline Control (n = 6) | 161 ± 48 | 9.9 × 10$^3$ ± 4.7 × 10$^3$ | 2.6 × 10$^2$ ± 1.1 × 10$^2$ | 17 ± 4 |
| CaSO$_4$ Control (n = 7) | 251 ± 78 | 2.1 × 10$^4$ ± 1.3 × 10$^4$ | 6.0 × 10$^2$ ± 3.7 × 10$^2$ | 26 ± 10 |
| 0.5 mg/kg ZnCl2 + CaSO$_4$ (n = 4) | 337 ± 175 | 3.0 × 10$^4$ ± 7.9 × 10$^3$ | 1.1 × 10$^2$ ± 9.4 × 10$^2$ | 36 ± 22 |

TABLE 6-continued

Four weeks post-fracture mechanical testing with formulation of zinc chloride (ZnCl$_2$) with CaSO$_4$ carrier applied to the fracture site.

| | | | | |
|---|---|---|---|---|
| 1.0 mg/kg ZnCl2 + CaSO$_4$ (n = 7) | 396 ± 112* | 3.9 × 10$^4$ ± 1.4 × 10$^{4*,\#}$ | 1.3 × 10$^3$ ± 7.1 × 10$^{2*}$ | 46 ± 16* |
| 3.0 mg/kg ZnCl2 + CaSO$_4$ (n = 5) | 262 ± 126 | 2.1 × 10$^4$ ± 7.8 × 10$^3$ | 7.0 × 10$^2$ ± 3.1 × 10$^2$ | 33 ± 19 |

Fractured Femur Calues Normalized to the Contralateral (Intact) Femur

| | Percent Maximum Torque to Failure | Percent mazimum Torsional Rigidity | Percent Effective Shear Modulus | Percent Effective Shear Stress |
|---|---|---|---|---|
| Saline Control (n = 6) | 27 ± 18 | 20 ± 10 | 4 ± 2 | 10 ± 5 |
| CaSO$_4$ Control (n = 7) | 48 ± 21 | 55 ± 35 | 11 ± 7 | 16 ± 7 |
| 0.5 mg/kg ZnCl2 + CaSO$_4$ (n = 4) | 56 ± 31 | 63 ± 20 | 17 ± 19 | 19 ± 12 |
| 1.0 mg/kg ZnCl2 + CaSO$_4$ (n = 7) | 75 ± 18* | 79 ± 32* | 18 ± 10 | 27 ± 8* |
| 3.0 mg/kg ZnCl2 + CaSO$_4$ (n = 5) | 45 ± 22 | 52 ± 22 | 14 ± 8 | 20 ± 14 |

The data represents average values ± standard deviation
*Represents values statistically higher than saline control, p < 0.05 versus saline control.
Represents values statistically higher than CaSO4 control, p < 0.05 versus CaSO4 control.
One-way ANOVA between 5 groups with Holm-Sidak post-hoc analysis Table 6 summarizes the results of the mechanical testing of the bone for fractured bone, following four weeks of healing using the formulation. The effective shear stress was 2.7× and 1.7× higher at four weeks post-fracture for the healing femurs from the ZnCl$_2$/CaSO$_4$ treated animals, at dosages of 1.0 mg/kg compared to saline and CaSO$_4$ control, respectively. When normalized to their intact, contralateral femurs, the percent maximum torque to failure, percent torsional rigidity, and percent effective shear modulus, of the fractured femora were 2.8×, 4.0×, and 4.5× higher, respectively, at the dosage of 1 mg/kg ZnCl$_2$ CaSO$_4$ compared to the saline control group (p<0.05).

Comparison of Use of ZnCl$_2$ with Existing Therapy (BMP2)

As an insulin-mimetic adjunct, zinc compounds can be used to accelerate bone regeneration by stimulating insulin signaling at the fracture site. ZnCl$_2$ treatment applied directly to the fracture site significantly increased the mechanical parameters of the bone in treated animals after four weeks, compared to controls. It accelerated fracture-healing process (fracture healing resolved in four to five weeks, instead of average eight to ten weeks in standard rat femur fracture model).

Other healing adjuncts currently approved for FDA use in the United States include Bone Morphogenic Proteins (BMP's) and Exogen/Pulsed Electromagnetic Fields (PEMF). However, BMPs may be associated with shortcomings such as causing ectopic bone growth and having high cost per application; and Exogen/PEMF therapy has shown only limited proven usefulness in fracture healing and needs for patient compliance for daily use.

Figure 6:
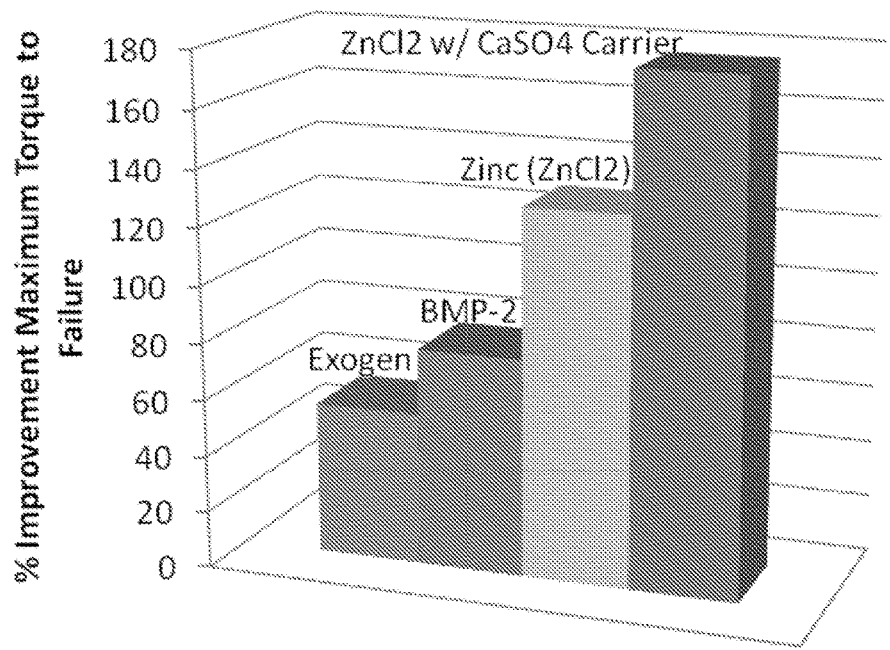
FIG. 6 illustrates comparison of use of $ZnCl_2$ with the existing therapy (BMP2): (1) a single intramedullary dose (1 mg/kg) of $ZnCl_2$ with the calcium sulfate ($CaSO_4$) vehicle (purple); (2) a single intramedullary dose (3 mg/kg) of $ZnCl_2$ without a vehicle (green); (3) BMP-2 study used a single percutaneous dose of BMP-2 (80 μg) with buffer vehicle (red); and (4) Exogen study used daily exposure periods of ultrasound treatment (20 mm/day). The average value (duration of 25 days) is shown in blue.

The chart in FIG. 6 compares the use of ZnCl$_2$ (alone or in combination with CaSO$_4$) with the currently approved products (BMP-2 and Exogen) for fracture healing. Each of these studies examined the effectiveness of a therapeutic adjunct on femur fracture healing by measuring the maximum torque to failure at the four week time point. Specifically the following were compared to their respective untreated control group: (1) a single intramedullary dose (1 mg/kg) of ZnCl2 with the calcium sulfate (CaSO4) vehicle (purple); (2) a single intramedullary dose (3 mg/kg) of ZnCl2 without a vehicle (green); (3) BMP-2 study used a single percutaneous dose of BMP-2 (80 mg) with buffer vehicle (red) (see Einhorn, T. A., et al., *J. Bone Joint Surg. Am.* 2003, 85-A(8):1425-1435); and (4) Exogen study used daily exposure periods of ultrasound treatment (20 mm/day). The average value (duration of 25 days) is shown in blue (see Azuma, Y., et al., *J. Bone Miner. Res.* 2001, 16(4):671-680.

As graphically shown, use of single application of insulin-mimetic like zinc chloride results in significantly increased improvement of torque to failure and other mechanical properties of the fracture callus, compared to the existing gold standard of LIPUS and BMP2, using torsional mechanical testing of rat femur fracture model of Bonnarrens and Einhorn.

In summary, we have found that acute, local ZnCl$_2$ treatment (either alone or as a formulation with a carrier), administered immediately prior to an induced fracture, promoted healing in non-diabetic rats. At the four week time point, mechanical parameters of the healed bone were substantially higher than that of the control group. This is consistent with our earlier findings of insulin's ability to promote bone growth when applied to the fracture site. This is also consistent with our finding that insulin mimetic compounds such as vanadyl acetylacetonate (VAC) accelerate fracture healing much like insulin. Though also an insulin mimetic, unlike VAC. ZnCl$_2$ is a compound commonly used in many commercial medical products and hence potential regulatory barriers are minimal. This suggests that insulin mimetics applied locally to the fracture may be used therapeutically as a fracture-healing adjunct, and local ZnCl$_2$ treatment is a cost-effective fracture-healing adjunct and has potential for other possible orthopedic applications.

The above preliminary data indicate that local treatment with an insulin-mimetic such as zinc is an effective method to enhance bone regeneration. Mechanical parameters and radiography revealed that bone bridged at four weeks after fracture in the zinc-treated rats as compared to saline treated controls. Spiral fractures that occurred during mechanical testing support the radiographic observations and suggest that local ZnCl$_2$ application at the dosages tested may accelerate fracture healing, compared to untreated controls. These data support additional testing of ZnCl$_2$ as a therapeutic agent to accelerate or enhance bone regeneration.

Example 2

Use of Manganese Compounds for Fracture Healing

Material and Methods
Rat Model

The animal model used for this study is the Diabetes Resistant (DR) BB Wistar Rat. It will be obtained from a breeding colony at UMDNJ-New Jersey Medical School (NJMS) which is maintained under controlled environmental conditions and fed ad libitum.

The BB Wistar colony was established from diabetic-prone BB Wistar rats originally obtained from BioBreeding (Toronto, Canada). Similar to human type I diabetes, spontaneously diabetic BB Wistar rats display marked hyperglycemia, glycosuria and weight loss within a day of onset, associated with decreased plasma insulin after undergoing selective and complete destruction of pancreatic β-cells. If left untreated, diabetic BB Wistar rats would become ketoacidic within several days, resulting in death. Genetic analysis of the BB-Wistar rat shows the development of diabetes is strongly related to the presence of the iddm4 diabetogenic susceptibility locus on chromosome 4 as well as at least four other loci related to further susceptibility and the development of lymphopenia (Martin, A. M., et al., *Diabetes* 1999, 48(11):2138-41).

The DR-BB Wistar rat colony was also originally purchased from BioBreeding and has been established as an effective control group for studies involving the diabetic BB Wistar rat. Under controlled environmental conditions, DR-BB Wistar rats would never develop spontaneous type I diabetes, are non-lymphopenic, and are immunocompetent. It has since been used in our lab as a model of a "normal" rat model. The choice was made to utilize the DR-BB Wistar rat, rather than purchase commercially available rats for our studies, because of the ability to expand the colony by breeding at any time as necessary for different protocols, as well our familiarity with the rat over years of its utilization in similar protocols. The consistent use of the BB Wistar and the DR-BB Wistar rat models allow for an increase in reliability when comparing data between our various protocols.

General Health of Animals

The age of the BB Wistar rats at the time of fracture surgery varied between 95 and 137 days. However, animals amongst treatment groups were age and sex matched for each experiment. The percent weight change following surgery to the day of sacrifice was similar amongst treatment groups.

Surgical Technique

Surgery will be performed to produce a closed mid-diaphyseal fracture model in the right femur. General anesthesia will be administered prior to surgery by intraperitoneal (IP) injection of ketamine (60 mg/kg) and xylazine (8 mg/kg). The right leg of each rat is shaved and the incision site is prepared with Betadine and 70% alcohol. A one centimeter medial, parapatellar skin incision is made, followed by a smaller longitudinal incision through the quadriceps muscle, just proximal to the quadriceps tendon. The patella is dislocated laterally and the intercondylar notch of the distal femur is exposed. An entry hole is made with an 18-gauge needle and the femoral intramedullary canal is subsequently reamed. For experimental groups, 0.1 mL of MnCl2 solution(of different dosage) is injected into the medullary canal of the femur. For control groups, 0.1 mL of saline is injected. A Kirschner wire (316LVM stainless steel, 0.04 inch diameter, Small Parts, Inc., Miami Lakes, Fla.) is inserted into the intramedullary canal. The Kirschner wire is cut flush with the femoral condyles. After irrigation, the wound is closed with 4-0 vicryl resorbable sutures. A closed midshaft fracture is then created unilaterally with the use of a three-point bending fracture machine. X-rays are taken to determine whether the fracture is of acceptable configuration. Only transverse, mid-diaphyseal fractures are accepted. The rats are allowed to ambulate freely immediately post-fracture.

Post Surgery Procedures

X-rays are taken at two-week intervals to the day of euthanasia. After euthanasia x-rays are taken as well. To take x-rays, animals will be given a half dose of anesthesia. All groups will be monitored closely for four days after surgery for infection, and the ability to ambulate freely.

Torsional Mechanical Testing

Torsional testing was conducted at 4 weeks post-fracture, using a servohydraulics machine (MTS Sys. Corp., Eden Prairie, Minn.) with a 20 Nm reaction torque cell (Interface, Scottsdale, Ariz.), Femurs were tested to failure at a rate of 2.0 deg/sec at four weeks post-fracture. The peak torque, torsional rigidity, effective bulk modulus, and the effective maximum shear stress (σ) were determined with standard equations that model each femur as a hollow ellipse (Ekeland. A. et al., *Acta Orthop, Scand.* 1981, 52(6):605-613; Engesaeter, L. B. et al., *Acta Orthop. Scand* 1978, 49(6): 512-518). In order to compare the biomechanical parameters between different groups, the data was normalized by dividing each fractured femur value by its corresponding intact, contralateral femur value. Torsional mechanical testing is limited by differences in gauge length during bone potting in Field's metal. Placement and dimension of fracture gap can contribute to standard deviations. Finally, this test is limited because it relies on a mathematical model that assumes the femur is a hollow ellipse, as opposed to the natural architecture of femoral bone (Levenston, M. E., et al., *J. Bone Miner. Res.* 1994, 9(9):1459-1465).

Early-Stage Healing Analysis by Histomorphometry

The fractured femora were resected at seven and ten clays post-fracture, decalcified, dehydrated, embedded in paraffin, and sectioned using standard histological techniques. Sections were stained with Masson's Trichrome (Accustain™ Trichrome Staining kit, Sigma Diagnostics, St. Louis, Mo.) for histological observation using an Olympus BH2-RFCA microscope (Olympus Optical Co., Ltd., Shinjuku-ku, Tokyo, Japan). Digital images were collected using a Nikon DXM1200F digital camera (Nikon, Tokyo, Japan). Cartilage, new bone, and total callus area were measured from the digital images using Image-Pro Plus software (version 5, Media Cybernetics, Inc., Silver Spring, Md.). Total cartilage and new bone area were normalized to total callus area and expressed as the percent area. Two independent reviewers were used to minimize inconsistencies.

Data and Statistical Analysis

Analysis of variance (ANOVA) was performed followed by Holm-Sidak post-hoc tests to determine differences between the treated $MnCl_2$ groups with a group size larger than two. A Student's t-test was performed to identify differences between the two treated groups in the $MnCl_2$ study (SigmaStat 3.0, SPSS Inc., Chicago, Ill.). A p value less than 0.05 was considered statistically significant.

Results

Mechanical Testing

Local $MnCl_2$ No Carrier

The effect of local MnCl2 therapy on healing of femur fractures was measured by torsional mechanical testing. At four weeks post-fracture, rats treated with $MnCl_2$ displayed improved mechanical properties of the fractured femora compared to the saline control group. The maximum torque to failure was significantly increased compared to the saline control group ($p<0.05$: 0.125 mg/kg $MnCl_2$, $p<0.05$: 0.25 mg/kg $MnCl_2$, $p<0.05$: 0.3 mg/kg $MnCl_2$) (Table 7). When the mechanical parameters of the fractured femora were normalized to the intact, contralateral femora, percent torsional rigidity was significantly greater in the local $MnCl_2$ treated groups when compared to the saline control group ($p<0.05$: 0.125 mg/kg $MnCl_2$, $p<0.05$: 0.25 mg/kg $MnCl_2$)) (Table 7).

Histomorphometric Analysis

In animals treated with MnCl2, histomorphometric analysis revealed a statistically lower ($p<0.05$) percent cartilage in 0.3 mg/kg Mn Cl2 treated femora, compared to controls at seven days (Table 8). At ten days, percent mineralized tissue in 0.3 mg/kg Mn Cl2 treated femora were significantly increased ($p<0.05$: 0.3 mg/kg Mn Cl2) compared to saline controls (Table 8).

TABLE 7

Four weeks post-fracture mechanical testing with local manganese chloride ($MnCl_2$)

Fractured Femur Values

| | Maximum Torque to Failure (Nmm) | Maximum Torsional Rigidity (Nmm$^2$/rad) | Effective Shear Modulus (MPa) | Effective Shear Stress (MPa) |
|---|---|---|---|---|
| Saline Control (n = 6) | 161 ± 48 | $9.9 \times 10^3 \pm 4.7 \times 10^3$ | $2.6 \times 10^2 \pm 1.1 \times 10^2$ | 17 ± 4 |
| 0.083 mg/kg $MnCl_2$ (n = 5) | 272 ± 39 | $2.6 \times 10^4 \pm 1.2 \times 10^4$ | $8.7 \times 10^2 \pm 4.9 \times 10^2$ | 30 ± 8 |
| 0.125 mg/kg $MnCl_2$ (n = 4) | 351 ± 59* | $4.2 \times 10^4 \pm 1.1 \times 10^4$ | $6.4 \times 10^2 \pm 8.8 \times 10^1$ | 21 ± 6 |
| 0.25 mg/kg $MnCl_2$ (n = 4) | 344 ± 84* | $3.4 \times 10^4 \pm 1.6 \times 10^4$ | $8.1 \times 10^2 \pm 5.0 \times 10^2$ | 32 ± 11 |
| 0.30 mg/kg $MnCl_2$ (n = 6) | 323 ± 135* | $3.0 \times 10^4 \pm 2.6 \times 10^4$ | $7.6 \times 10^2 \pm 9.2 \times 10^2$ | 27 ± 23 |
| 0.50 mg/kg $MnCl_2$ (n = 6) | 230 ± 83 | $2.9 \times 10^4 \pm 1.2 \times 10^4$ | $6.2 \times 10^2 \pm 3.5 \times 10^2$ | 19 ± 9 |

Fractured Femur Values Normalized to the Contralateral (Intact) Femur

| | Percent Maximum Torque to Failure | Percent maximum Torsional Rigidity | Percent Effective Shear Modulus | Percent Effective Shear Stress |
|---|---|---|---|---|
| Saline Control (n = 6) | 27 ± 18 | 20 ± 10 | 4 ± 2 | 10 ± 5 |
| 0.083 mg/kg $MnCl_2$ (n = 5) | 42 ± 5 | 56 ± 30 | 8 ± 7 | 8 ± 4 |
| 0.125 mg/kg $MnCl_2$ (n = 4) | 54 ± 5 | 103 ± 40* | 16 ± 11 | 14 ± 5 |
| 0.25 mg/kg $MnCl_2$ (n = 4) | 55 ± 19 | 80 ± 34* | 14 ± 9 | 16 ± 6 |
| 0.30 mg/kg $MnCl_2$ (n = 6) | 50 ± 22 | 50 ± 37 | 10 ± 12 | 16 ± 12 |
| 0.50 mg/kg $MnCl_2$ (n = 6) | 38 ± 15 | 61 ± 16 | 17 ± 13 | 14 ± 7 |

The data represents average values ± standard deviation
*Represents values statistically higher than saline control, $p < 0.05$ versus saline control.

Radiographic Analysis

Radiographs taken at four weeks post-fracture support these mechanical testing results (FIG. 7). At four weeks, the fractures treated with 0.25 mg/kg dosage of $MnCl_2$ displayed increased mineralized tissue than saline controls. Additionally, analysis of radiographs showed the $MnCl_2$ group demonstrated union at the subperiosteal bony area and at the callus, whereas saline control radiographs had no evidence of union.

TABLE 8

Histology: comparison of manganese chloride with saline control

| Group | 7 days post fracture | | 10 days post fracture | |
|---|---|---|---|---|
| | % cartilage | % new bone | % cartilage | % new bone |
| Saline | 6.116 ± 2.51 | 15.668 ± 2.93 | 9.542 ± 1.02 | 14.011 ± 1.29 |
| 0.3 mg/kg | 2.859 ± 1.09 # | 15.604 ± 2.39 | 11.051 ± 3.05 | 18.866 ± 2.28 * |

* Represents values statistically higher than saline control, $p < 0.001$
Represents values statistically lower than saline control, $p < 0.05$

Example 3

Use of Vanadium Compounds for Bone Fracture Healing

Method
General Description of Animal Surgery

A closed mid-diaphyseal fracture surgery was performed on the right femur of each rat as described previously. General anesthesia was administered by intraperitoneal injection of ketamine (60 mg/kg) and xylazine (8 mg/kg). A closed, midshaft fracture was then created using a three-point bending fracture instrument (BBC Specialty Automotive, Linden N.J.) and confirmed with X-rays immediately post-fracture.

Preparation of VAC Solution

Vanadyl acetylacetonate (VAC), Sigma Aldrich, St. Louis, Mo., mixed with sterile water at various doses with or without a calcium sulfate carrier, were injected into the intramedullary canal prior to fracture. VAC was chosen over alternative organo-vanadium compounds such as BMOV and VS, due to its' observed superior potency at stimulating protein kinase B (PKB). Glycogen synthase kinase 3 beta (GSK-3β), and protein tyrosine phosphorylation (PTP). Additionally, Mehdi et al. noted more potent Insulin receptor beta subunit (IRβ), and Insulin receptor substrate 1 (IRS-1) tyrosine phosphorylation, for VAC, compared to BMOV and VS. Doses of VAC were not based on each animal's body weight, but on a lower theoretically tolerable dose for a 290 gram BB Wistar rat, which would not elicit heavy metal poisoning or behavioral changes. This weight is over 50 grams lower than the average weight of non-diabetic BB Wistar rats at an age of approximately 90 days (the age of investigation in this study). The daily subcutaneous dose injected by Zhang et al. (3 mg VAC/kg body weight) was multiplied by this average weight of 0.29 kg. A 0.1 mL volume of the VAC solution was administered locally via a single injection into the marrow space for each dose examined. This reduced the absolute concentration of VAC administered in the high dose to the same concentration as Zhang et al., while the 1.5 mg/kg dose was 50% of the dose administered by Zhang. Later the 0.5 mg/kg dose (33.3% of low dose) and 0.25 mg/kg dose (16.6% of low dose) were evaluated to determine the optimal dose of VAC, and examine the range of effectiveness of VAC.

Preparation of VAC/CaSO$_4$ Formulation

To prepare the CaSO$_4$-VAC mixture, two grams of CaSO$_4$ were placed in glass vials. The vials were placed in an autoclave and sterilized at for two hours in a dry cycle. CaSO$_4$ powder (0.8 grams) was mixed with 400 µl of saline or 400 µl of VAC solution (0.25 mg/kg and 1.5 mg/kg) for one minute at room temperature. The mixture was packed into the barrel of a 1 cc sterile syringe and pushed down into the open orifice of the syringe barrel by insertion of the syringe plunger. After attaching an 18-gauge sterile needle to the syringe barrel, 0.1 ml volume of the mixture was directly injected into the rat femoral canal (non-diabetic BB Wistar rat) prior to Kirschner wire insertion and fracture.

Pack Boriding (Vanadium-Boron and Boron Control) Stainless Steel Rod Manufacturing:

During boriding of steel and other metallic and alloy surfaces, boron atoms diffuse into the material and form various types of metal borides.

A 1.6 mm Kirschner wire was annealed, cleaned and packed in a boriding powder mixture contained within a 5 mm thick, heat resistant steel box. This allows the surfaces to be borided with a layer that is 10-20 micrometers thick. A mixture was made consisting of boron carbide, VAC, silicon carbide, and a boriding activator. The parts conformed to the container which they were packed, and then covered with a lid, which rests inside the container. This container was then weighted with an iron slug to ensure even trickling of the boriding agent during the manufacturing. The container was then heated to the boriding temperature in an electrically heated box with covered heating coils. The coated rods were allowed to come to room temperature and wiped with 95% ethyl alcohol prior to surgery for sterilization.

Vanadium Quantification in Animal Models

BB Wistar rats were anesthetized and confirmed to be non-responsive to external stimuli before beginning the surgical procedure. The anesthetized rat was be exsanguinated by cardiac puncture using a 10 ml syringe with a 22 gauge needle after shallow puncture just lateral to the sternum and through the intercostal space. After puncturing the dermis and cardiac wall slight backpressure was placed on the plunger to withdraw blood from the ventricle. The collected blood was transferred to an appropriate container used for collection of plasma (heparinized) or serum (non-heparinized). Following the cardiac puncture, the rats were euthanized via cervical dislocation.

The excised femora were be stripped of adhering muscle, tendon and other tissue after which the bones were rinsed three times with deionized water, and then placed on glassine paper and air dried. The pin was rinsed once and stored in a clean conical tube. The liver, kidneys, brain, and left humerous collected were rinsed 3× and air dried. The objective of "drying" was to remove adhering water droplets after the water rinse and to allow the true tissue weight to be recorded as precisely as possible. The tissue's location on the glassine paper was changed after a minute or two of air exposure. Air-drying does not last longer than 5 minutes. The dry bone is placed into a dry, previously acid-soaked/deionized-water rinsed, 7 ml pre-weighed sealable scintillation vial with plastic liner cap. Other organs were also stored in pre-rinsed, dry pre-weighed plastic vials of sizes appropriate for each. The vials were labeled with an indelible marker indicating the date of collection, right or left femur, Rat ID code, Investigator and Study ID. The organs were then placed into a low temperature (−80 degrees Celsius) freezer for storage until future analysis (quantification not currently planned).

The bone was carefully air-dried and any entrained fluid in the endosteal space drawn or shaken out to avoid bone weight anomaly. Beakers for subsequent collections were re-cleaned and femurs were handled carefully to avoid cross contamination of specimens. Bones were analyzed via atomic absorption spectrophotometry to determine levels of vanadium in bone, compared to standard levels in normal rat femoral bone. Analysis was based on a standard published technique 14 for quantifying vanadium levels in tissues.

Early-Stage Healing Analysis by Histomorphometry

The fractured femora were resected at 2, 4, 7, and 10 days post-fracture, decalcified, dehydrated, embedded in paraffin, and sectioned using standard histological techniques. Sections were stained with Masson's Trichrome (Accustain™ Trichrome Staining kit, Sigma Diagnostics, St. Louis, Mo.) for histological observation using an Olympus BH2-RFCA microscope (Olympus Optical Co., Ltd., Shinjuku-ku, Tokyo, Japan). Digital images were collected using a Nikon DXM1200F digital camera (Nikon, Tokyo, Japan). Cartilage, new bone, and total callus area were measured from the digital images using Image-Pro Plus software (version 5, Media Cybernetics, Inc., Silver Spring, Md.). Total cartilage and new bone area were normalized to total callus area and expressed as the percent area. Two independent reviewers were used to minimize inconsistencies.

Late-Stage Healing Analysis by Histomorphometry

To examine the effects of VAC at later stages of fracture healing, femora were resected from animals in the groups described above at days 10, 14, and 21, embedded and sectioned using standard histological techniques. This includes dehydration, soaking in Xylenes, and finally pre-embedding in a layer of Polymethylmethacrylate (PMMA). After embedding in pure PMMA and allowed to solidify in a hot water bath, slides were sectioned from the PMMA blocks, polished, and stained with a combination of Stevenel's blue and Van Gieson picro-fuchsin (SVG). Histological images of fracture calluses were obtained using an Olympus SZX12 upright microscope (Olympus Optical Co, LTD, Japan) connected via a CCD camera (Optronics, Goleta, Calif.) to a personal computer and analyzed with the Bioquant software package (Biometrics, Inc, Nashville, Tenn.). Parameters that were compared include a) callus area, b) percent calcified tissue area, and c) percent cartilage area. Limitations of this procedure include production of slides with high thicknesses, due to the difficulties associated with sectioning PMMA. This limits the number of possible sections that may be cut for staining in addition to analysis of cellular morphology, due to overlapping layers of cells.

Early Immunohistochemistry

At days 2, 4, and 7, and 10, animals were injected intraperitoneally with 30 mg/kg of 5-bromo-2'deoxyuridine (BrdU, Sigma Chemical Co., St. Louis, Mo.) one hour prior to sacrifice to label replicating cells as a measure of cellular proliferation. The fractured femurs were resected and fixed in formalin, decalcified (Immunocal, Decal Corp., Tallman, N.Y.), embedded in paraffin, and sectioned longitudinally (5 μm thick). Cells positive for BrdU incorporation were detected by immunohistochemistry using commercially available reagents (DAKO Corp., Carpentaria, Calif.). Digital images of each fracture were collected with an Olympus BH2-RFCA microscope equipped with a Nikon DXM1200f camera. For each specimen, callus area was measured and the BrdU positive cells in the periosteal callus region were counted using Image Pro Plus software. All BrdU positive cells in the external callus to a maximum of 1 cm proximal and distal of the fracture site and 3 mm from the external surface of the femur were counted. The number of BrdU positive cells was normalized per unit area of callus and only one datum per rat (BrdU positive cells per mm2) was used for the statistical analysis.

Torsional Mechanical Testing

Torsional testing was conducted at weeks four and five using a servohydraulics machine (MTS Sys. Corp., Eden Prairie, Minn.) with a 20 Nm reaction torque cell (Interface, Scottsdale, Ariz.). Femurs were tested to failure at a rate of 2.0 deg/sec at four and six week time points. The peak torque, torsional rigidity, effective bulk modulus, and the effective maximum shear stress (a) were determined with standard equations that model each femur as a hollow ellipse. In order to compare the biomechanical parameters between different groups, the data was normalized by dividing each fractured femur value by its corresponding intact, contralateral femur value. Torsional mechanical testing is limited by differences in gauge length during bone potting in Field's metal Placement and dimension of fracture gap can contribute to standard deviations. Finally, this test is limited because it relies on a mathematical model that assumes the femur is a hollow ellipse, as opposed to the natural architecture of femoral bone.

Data and Statistical Analysis

Analysis of variance (ANOVA) was performed followed by Holm-Sidak post-hoc tests to determine differences between the treated VAC groups with a group size larger than two. A Student's t-test was performed to identify differences between the two treated groups in the VAC study (SigmaStat 3.0, SPSS Inc., Chicago, Ill.). A p value less than 0.05 was considered statistically significant.

General Health of Animals

The age of the BB Wistar rats at the time of fracture surgery varied between 75 and 137 days. However, animals amongst treatment groups were age and sex matched for each experiment. The percent weight change following surgery to the day of sacrifice was amongst treatment groups.

Results

Vanadium Quantification in Animal Models

Figure 8:
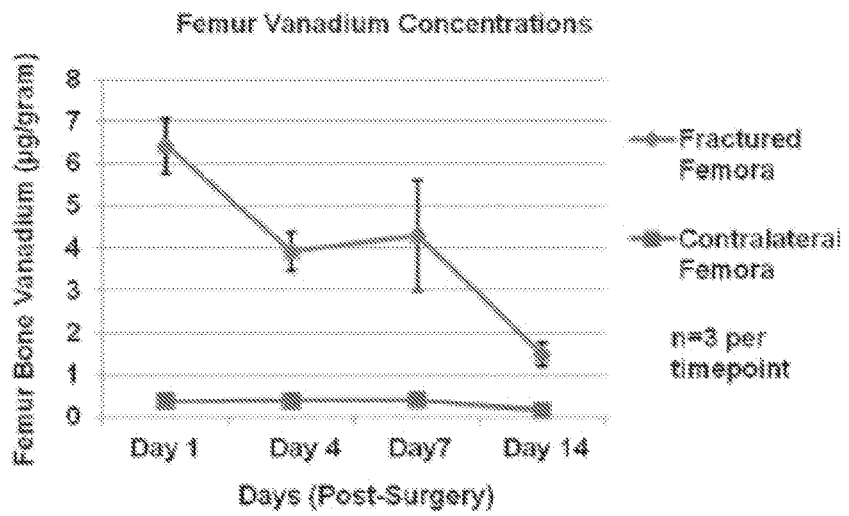
FIG. 8 illustrates quantification of local VAC levels. Femur bone vanadium concentrations (μg vanadium/gram of bone mass) at one, four, seven, and fourteen days after surgery for fractured and contralateral (intact) femora.

Locally injected VAC remains bound within the fractured femora approximately two weeks after local injection. These results were determined from the following experiment. Immediately prior to fracture, the femoral canal of each rat was injected with 0.1 ml of either saline or 4.35 mg/mL of VAC solution (4.35 mg/ml VAC solution; approximately 1.5 mg VAC/kg weight of the rat; approximately 435 μg of VAC powder; approximately 84 μg of vanadium). To assess how rapidly the vanadium disperses from the fracture site, rats were sacrificed at one, four, seven, and 14 days after surgery to measure vanadium levels in the fracture callus. Atomic absorption spectrophotometry was used to quantify local vanadium levels and normalized compared to levels in normal rat femur bone. Significant differences ($p<0.05$) in local vanadium levels were detected between the right, fractured femora and left, non-fractured femora of the rats treated with local vanadium at all time points examined (FIG. 8). The half-life of VAC is relatively short (6 days) according to Zhang et al and the quantity within the fractured femora significantly decreased at four, seven, and 14 days compared to the contralateral femora. At 14 days, the local level of vanadium was significantly decreased ($p<0.05$) compared to days one, four, and seven.

Histomorphometric Analysis

Figure 9:
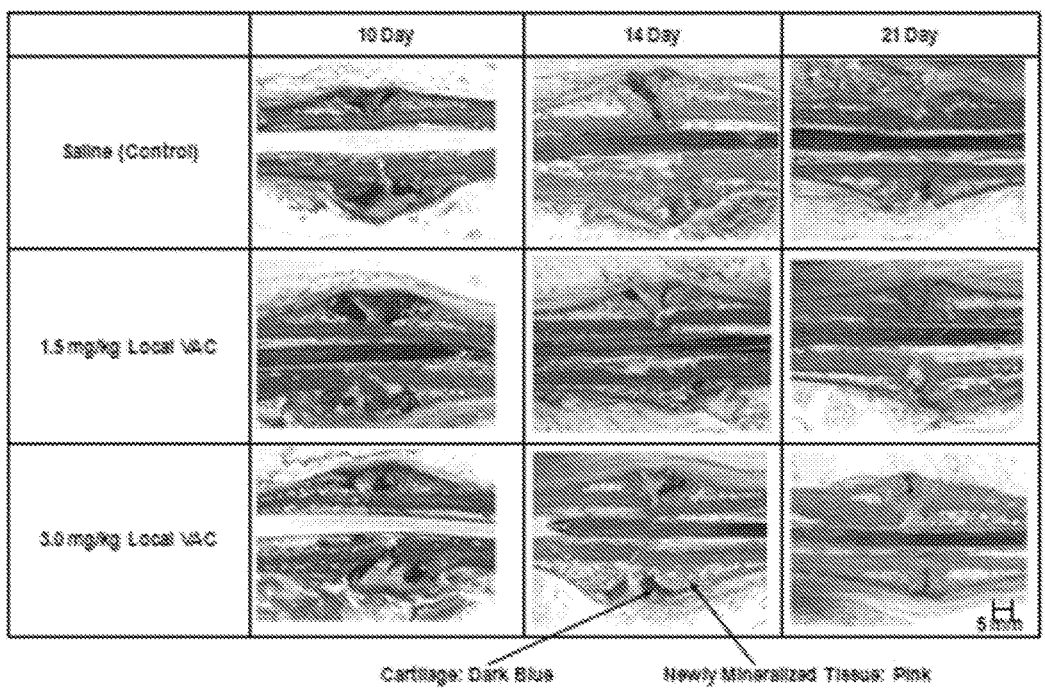
FIG. 9 illustrates histological comparison between VAC and saline control treated rats: Representative sections of saline control, 1.5 mg/kg VAC, and 3 mg/kg VAC groups show progression of healing from 10-21 days at 1.67× as visualized under stereomicroscope.

In animals treated with VAC, histomorphometric analysis revealed a statistically higher ($p<0.05$) percent cartilage in 1.5 mg/kg VAC treated femora, compared to controls at both 7 and 10 days (Table 9). At 14 days, percent mineralized tissue in both 1.5 mg/kg and 3 mg/kg VAC treated femora were significantly increased ($p<0.05$:1.5 mg/kg VAC, $p<0.05$: 3 mg/kg VAC) compared to saline controls (Table 9). After 21 days, percent mineralized tissue was significantly increased ($p<0.05$) in 1.5 mg/kg VAC treated femora. This VAC-mediated acceleration of healing may be seen via histological sections at clays 10-21 (Table 9 FIG. 9).

TABLE 9

Late histology local VAC delivery without a carrier in normal rats

| | 10 Days Post-Fracture | | | 14 Days Post-Fracture | | |
|---|---|---|---|---|---|---|
| | Callus Area | % Mineralized | % | Callus Area | % Mineralized | % |

TABLE 9-continued

Late histology local VAC delivery without a carrier in normal rats

|  | (mm²) | Tissue | Cartilage | (mm²) | Tissue | Cartilage |
|---|---|---|---|---|---|---|
| Saline Control | 15.8 ± 2.3 (n = 5) | 17.9 ± 5.2 (n = 5) | 16.3 ± 2.8 (n = 5) | 19.5 ± 4.8 (n = 6) | 15.6 ± 4.7 (n = 6) | 12.4 ± 4.9 (n = 6) |
| 1.5 mg/kg VAC | 18.4 ± 3.6 (n = 7) | 15.8 ± 5.1 (n = 7) | 30.6 ± 12.4* (n = 7) | 21.7 ± 5.0 (n = 5) | 21.3 ± 2.1* (n = 5) | 14.2 ± 4.9 (n = 5) |
| 3.0 mg/kg VAC | 18.6 ± 2.9 (n = 5) | 15.2 ± 3.4 (n = 5) | 17.8 ± 5.5 (n = 5) | 19.3 ± 3.1 (n = 5) | 21.9 ± 3.2* (n = 5) | 13.0 ± 6.4 (n = 5) |

| 21 Days Post-Fracture | | |
|---|---|---|
| Callus Area (mm²) | % Mineralized Tissue | % Cartilage |

|  | Callus Area (mm²) | % Mineralized Tissue | % Cartilage |
|---|---|---|---|
| Saline Control | 20.0 ± 6.8 (n = 6) | 25.0 ± 6.1 (n = 6) | 6.1 ± 3.2 (n = 6) |
| 1.5 mg/kg VAC | 20.1 ± 4.5 (n = 5) | 32.7 ± 2.9* (n = 5) | 11.0 ± 4.7 (n = 5) |
| 3.0 mg/kg VAC | 20.3 ± 5.1 (n = 4) | 33.4 ± 5.2 (n = 4) | 9.4 ± 5.7 (n = 4) |

The data represent mean values (±S.D.).
*Represents values statistically higher than saline control, $p < 0.05$ versus saline control.

Early Immunohistochemistry

In animals treated with VAC, no significant differences in cell proliferation existed at two or four days post-fracture, but significantly more proliferating cells per unit area ($p<0.05$) was observed in the periosteum at seven and ten days post-fracture.

Mechanical Testing

Local VAC Without a Carrier

Figure 10:
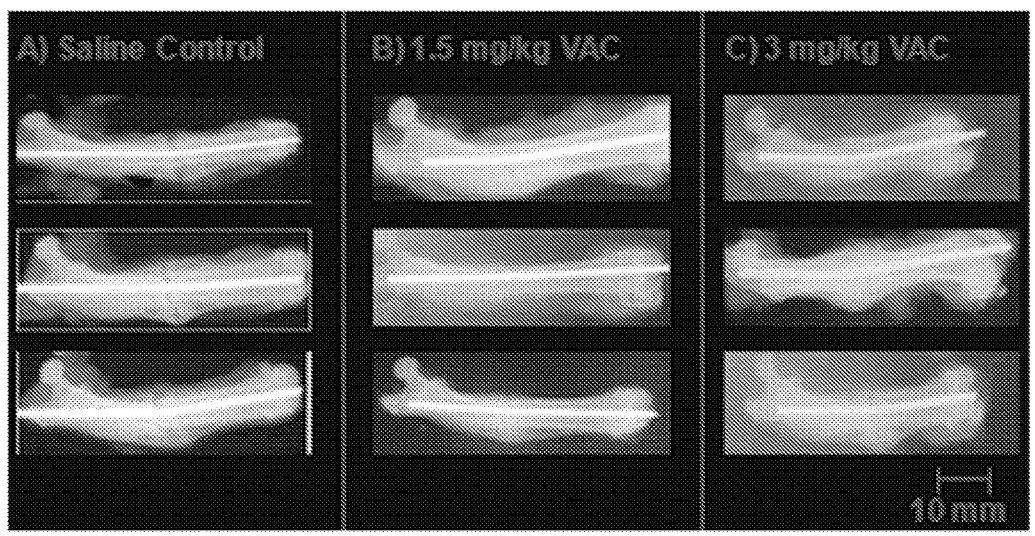
FIG. 10 illustrates 4-week radiographs of three representative samples for each group of fractured femur hones: (A) saline control, (B) 1.5 mg/kg VAC, (C) 3.0 mg/kg VAC.

The effect of local vanadium therapy on healing of femur fractures was measured by torsional mechanical testing. At four weeks post-fracture, rats treated with vanadium displayed improved mechanical properties of the fractured femora compared to the untreated group. The maximum torque to failure, torsional rigidity, maximum effective shear stress, and effective shear modulus were all significantly increased compared to the untreated group ($p<0.05$: 1.51 mg/kg VAC, $p<0.05$: 3 mg/kg VAC) (Table 10). Radiographs taken at four weeks post-fracture support these mechanical testing results (FIG. 10). When the mechanical parameters of the fractured femora were normalized to the intact, contralateral femora, percent maximum torque to failure, percent torsional rigidity, and percent effective shear modulus were still significantly greater in the local vanadium treated groups when compared to the saline control group ($p<0.05$: 1.5 mg/kg VAC, $p<0.05$: 3 mg/kg VAC). By five weeks post-fracture the maximum torque to failure and torsional rigidity were significantly greater in the 1.5 mg kg VAC heated group compared to both control and 3 mg/kg VAC groups respectively ($p<0.05$) (Table 11).

TABLE 10

Post-fracture mechanical testing of vanadium (VAC) in normal rats at 4-weeks

|  | Maximum Torque to failure (Nmm) | Maximum Torsional Rigidity (Nmm²/rad) | Effective Shear Modulus (MPa) | Effective Shear Stress (MPa) |
|---|---|---|---|---|
| Control (n = 6) | 161 ± 48 | 9,889 ± 4,719 | 258 ± 108 | 17 ± 4 |
| 0.25 mg/kg VAC (n = 6) | 227 ± 64 | 28,218 ± 9,107 | 878 ± 416 | 25 ± 9 |
| 0.5 mg/kg VAC (n = 6) | 362 ± 49 *,# | 45,877 ± 13,079 * | 1,107 ± 441 | 32 ± 13 |
| 1.5 mg/kg VAC (n = 6) | 329 ± 117 * | 34,526 ± 16,851 * | 2,454 ± 2,370 * | 69 ± 59 * |
| 3.0 mg/kg VAC (n = 5) | 409 ± 43 *,# | 41,007 ± 11,236 * | 2,948 ± 1,218 * | 101 ± 18 *,#,& |

Fractured femur values normalized to the contralateral (intact) femur

|  | Percent maximum torque to failure | Percent maximum torsional rigidity | Percent Effective Shear Modulus | Percent Effective Shear Stress |
|---|---|---|---|---|
| Control (n = 6) | 27 ± 18 | 20 ± 10 | 4 ± 2 | 10 ± 5 |
| 0.25 mg/kg VAC (n = 6) | 49 ± 14 | 67 ± 21 * | 14 ± 4 | 10 ± 3 |

TABLE 10-continued

Post-fracture mechanical testing of vanadium (VAC) in normal rats at 4-weeks

| | | | | |
|---|---|---|---|---|
| 0.5 mg/kg VAC (n = 6) | 72 ± 19 * | 103 ± 23 *,# | 16 ± 7 | 20 ± 11 |
| 1.5 mg/kg VAC (n = 6) | 59 ± 28 | 76 ± 28 * | 23 ± 12 * | 26 ± 16 |
| 3.0 mg/kg (n = 5) | 79 ± 12 * | 78 ± 10 * | 20 ± 11 * | 30 ± 12 *,# |

The data represents average values ± standard deviation
* Represent values statistically higher than control, p < 0.05 versus control.
Represent values statistically higher than Extra Low Dose, p < 0.05 versus Extra Low Dose.
& Represent values statistically higher than Lowered Low Dose, p < 0.05 versus Lowered Low Dose.

TABLE 11

Post-fracture mechanical testing of VAC in normal rats at 5 weeks

Fractured femur values

| | Maximum Torque to failure (Nmm) | Maximum Torsional Rigidity (Nmm$^2$/rad) | Effective Shear Modulus (MPa) | Effective Shear Stress (MPa) |
|---|---|---|---|---|
| Control (n = 6) | 295 ± 164 | 20,111 ± 10,944 | 1,060 ± 693 | 45 ± 28 |
| 1.5 mg/kg VAC (n = 9) | 471 ± 91*,# | 34,522 ± 8,347* | 2,026 ± 924 | 75 ± 26 |
| 3.0 mg/kg VAC (n = 8) | 335 ± 89 | 37,496 ± 12,846* | 1,453 ± 683 | 43 ± 25 |

Fractured femur values normalized to the contralateral (intact) femur

| | Percent maximum torque to failure | Percent maximum torsional rigidity | Percent Effective Shear Modulus | Percent Effective Shear Stress |
|---|---|---|---|---|
| Control (n = 6) | 74 ± 42 | 80 ± 57 | 28 ± 29 | 31 ± 21 |
| 1.5 mg/kg VAC (n = 9) | 99 ± 17 | 103 ± 33 | 39 ± 26 | 47 ± 25 |
| 3.0 mg/kg VAC (n = 8) | 64 ± 26 | 98 ± 28 | 23 ± 9 | 22 ± 11 |

The data represents average value ± standard deviation
*Represent values shtistically higher than control, p < 0.05 versus control.
Represent values statistically higher than high dose, p < 0.05 versus high dose.

Local VAC Without a Carrier in Diabetic Model

The effect of local vanadium therapy on healing of diabetic femur fractures was measured by torsional mechanical testing. Blood glucose was monitored biweekly for type I diabetic BB Wistar rats and subcutaneous Linplants™ (Linshin, Canada) were administered to all diabetic animals, roughly every two weeks to maintain systemic glucose levels. At six weeks post-fracture diabetic rats treated with vanadium displayed significantly improved mechanical properties of the fractured femora compared to the untreated diabetic group. The maximum torque to failure, torsional rigidity, maximum effective shear stress, and effective shear modulus were all significantly increased compared to the untreated diabetic group (p<0.05: 1.5 mg/kg VAC) (Table 12). When the mechanical parameters of the fractured femora were normalized to the intact, contralateral femora, percent maximum torque to failure, percent torsional rigidity, percent effective shear stress, and percent effective shear modulus were still significantly greater in the local vanadium treated diabetic groups when compared to the untreated diabetic group (p<0.05: 1.5 mg/kg VAC). Torsional mechanical testing parameters for the VAC treated diabetic animals were comparable to the non-diabetic animals at six weeks.

TABLE 12

Post-fracture mechanical testing of non-diabetic, diabetic and diabetic rats treated with VAC at 6-weeks

| | Maximum Torque to failure (Nmm) | Maximum Torsional Rigidity (Nmm$^2$/rad) | Effective Shear Stress (MPa) |
|---|---|---|---|
| diabetic control (n = 23) | 154 ± 69 | 475 ± 259 | 3 ± 2 |
| 1.5 mg/kg VAC in diabetic (n = 3) | 410 ± 71 * | 43,089 ± 19,720 * | 98 ± 53 *,# |
| normal (n = 12) | 456 ± 66 * | 33,784 ± 11,849 * | 48 ± 16 * |

| Normalized to contralateral femur | Percent maximum torque to failure | Percent maximum torsional rigidity | Percent Effective Shear Stress |
|---|---|---|---|
| diabetic control (n = 23) | 27 ± 10 | 27 ± 15 | 8 ± 4 |
| 1.5 mg/kg VAC in diabetic (n = 3) | 85 ± 23 * | 136 ± 111 * | 33 ± 20 * |
| normal (n = 12) | 78 ± 15 * | 86 ± 29 | 28 ± 13 * |

The data represents average values ± standard deviation
* Represent values statistically higher than control, p < 0.05 versus control.
Represent values statistically higher than normal, p < 0.05 versus normal.
The value of the numbers for diabetic control is obtained from two papers of Gandhi (Insulin: Bone 2005; PRP: Bone 2006 and Beam et al 2002 JOR). The value of 6-week normal group is an average of Gandhi's paper and the investigator's 6 week mechanical test saline animals.

Local VAC/CaSO4 Formulations

When local vanadium with a calcium sulfate carrier was torsionally tested, results revealed significantly higher effective shear stress ($p<0.05$) for the 0.25 mg/kg VAC with calcium sulfate carrier group, compared to both the calcium sulfate buffer and 1.5 mg/kg VAC with calcium sulfite carrier groups. When the mechanical parameters of the fractured femora were normalized to the intact, contralateral femora, maximum torque to failure, and percent effective shear modulus were significantly greater in the 0.25 mg/kg VAC with calcium sulfate carrier group, compared to the calcium sulfate buffer group ($p<0.05$) (Table 13).

TABLE 13

Post-fracture mechanical testing of VAC/CaSO$_4$ in normal rats at 4-weeks

|  | Maximum Torque to failure (Nmm) | Maximum Torsional Rigidity (Nmm$^2$/rad) | Effective Shear Modulus (MPa) | Effective Shear Stress (MPa) |
| --- | --- | --- | --- | --- |
| Control (n = 6) | 161 ± 48 | 9,889 ± 4,719 | 258 ± 108 | 17 ± 4 |
| CaSO$_4$ Buffer (n = 9) | 241 ± 172 | 25,684 ± 20,795 | 680 ± 623 | 23 ± 16 |
| 0.25 mg/kg VAC and CaSO$_4$ Carrier (n = 6) | 430 ± 133 * | 31,138 ± 11,518 | 1,178 ± 484 * | 55 ± 21 *,#,& |
| 1.5 mg/kg VAC and CaSO$_4$ Carrier (n = 5) | 322 ± 157 | 26,302 ± 17,974 | 637 ± 395 | 29 ± 15 |

| Fractured femur values normalized to the contralateral (intact) femur | | | | |
| --- | --- | --- | --- | --- |
|  | Percent maximum torque to failure | Percent maximum torsional rigidity | Percent Effective Shear Modulus | Percent Effective Shear Stress |
| Control (n = 6) | 27 ± 18 | 20 ± 10 | 4 ± 2 | 10 ± 5 |
| CaSO$_4$ Buffer (n = 9) | 37 ± 30 | 47 ± 47 | 7 ± 7 | 9 ± 6 |
| 0.25 mg/kg VAC and CaSO$_4$ Carrier (n = 6) | 85 ± 24 *,# | 100 ± 49 * | 24 ± 10 *,#,& | 18 ± 9 |
| 1.5 mg/kg VAC and CaSO$_4$ Carrier (n = 5) | 64 ± 30 | 69 ± 47 | 15 ± 8 | 10 ± 7 |

The data represents average values ± standard deviation
* Represent values statistically higher than control, p < 0.05 versus control.
Represent values statistically higher than CaSO$_4$ Buffer, p < 0.05 versus CaSO$_4$ Buffer.
& Represent values statistically higher than Low Dose and CaSO$_4$ Carrier, p < 0.05 versus Low Dose and CaSO$_4$ Carrier.

Surface Modified VAC Coated Implants

Torsional mechanical testing of surface modified rods four weeks post-fracture demonstrated significantly greater maximum torque to failure for the animals with vanadium-boron surface modified rods compared to the group with untreated 316L stainless steel (SS) control rods ($p<0.05$). When the mechanical parameters of the fractured femora were normalized to the intact, contralateral femora, the percent maximum torque to failure was significantly greater for the animals with vanadium-boron surface modified rods compared to the group with untreated 316L stainless steel control rods ($p<0.05$). Although torsional mechanical parameters were higher for the vanadium-boron surface modified rods, compared to the boron surface modified control rods, no significant differences were found between these groups (Tables 14 and 15).

TABLE 14

Post-fracture mechanical testing on surface modified vanadium-bonded rods in normal rats (Pilot Data in Female Rats) at 4 weeks

| | Fractured femur values | | | |
| --- | --- | --- | --- | --- |
|  | Maximum Torque to failure (Nmm) | Maximum Torsional Rigidity (Nmm$^2$/rad) | Shear Modulus (MPa) | Maximum Shear Stress (MPa) |
| 316 L Stainless Steel Control Rod (n = 5) | 178 ± 38 | 9,363 ± 5,032 | 235 ± 102 | 19 ± 3 |

TABLE 14-continued

Post-fracture mechanical testing on surface modified vanadium-bonded rods in normal rats (Pilot Data in Female Rats) at 4 weeks

| | | | | |
|---|---|---|---|---|
| Boron Coated Control Rod (n = 3) | 251 ± 93 | 19,683 ± 9,207 | 1,909 ± 1,582 | 70 ± 46 |
| 0.6 mg/kg Vanadium-Boron Coated Rod (n = 4) | 305 ± 30 * | 31,078 ± 6,917 * | 2,347 ± 1,649 | 60 ± 33 |

Fractured femur values Normalized to the contralateral (intact) femur

| | Percent maximum torque to failure | Percent maximum torsional rigidity | Percent shear modulus | Percent maximum shear stress |
|---|---|---|---|---|
| 316 L Stainless Steel Control Rod (n = 5) | 30 ± 18 | 19 ± 11 | 4 ± 2 | 11 ± 5 |
| Boron Coated Control Rod (n = 3) | 68 ± 22 * | 73 ± 36 | 23 ± 18 | 33 ± 16 |
| 0.6 mg/kg Vanadium-Boron Coated Rod (n = 4) | 76 ± 9 * | 107 ± 36 * | 38 ± 19 * | 40 ± 20 * |

The data represents average values ± standard deviation
* Represent values statistically higher than control, $p < 0.05$ versus 316 L Stainless Steel control group.

TABLE 15

Post-fracture medianical testing with sm-face modified vanadium-bonded rods in normal rats (Study in Male Rats) at 4 weeks

| | Maximum Torque to failure (Nmm) | Maximum Torsional Rigidity, (Nmm$^2$/rad) | Effective Shear Modulus (MPa) | Effective Shear Stress (MPa) |
|---|---|---|---|---|
| 316 L Stainless Steel Control Rod (n = 6) | 161 ± 48 | 9,889 ± 4,719 | 258 ± 108 | 17 ± 4 |
| Boron Coated Control Rod (n = 3) | 269 ± 102 | 22,340 ± 12,323 | 400 ± 304 | 17 ± 8 |
| 0.6 mg/kg Vanadium-Boron Coated Rod (n = 5) | 366 ± 150 * | 23,650 ± 11,718 | 609 ± 422 | 32 ± 15 |

Fractured femur values normalized to the contralateral (intact) femur

| | Percent maximum torque to failure | Percent maximum torsional rigidity | Percent Effective Shear Modulus | Percent Effective Shear Stress |
|---|---|---|---|---|
| 316 L Stainless Steel Control Rod (n = 6) | 27 ± 18 | 20 ± 10 | 4 ± 2 | 10 ± 5 |
| Boron Coated Control Rod (n = 5) | 45 ± 20 | 51 ± 34 | 7 ± 6 | 10 ± 6 |
| 0.6 mg/kg Vanadium-Boron Coated Rod (n = 5) | 65 ± 25 * | 52 ± 25 | 9 ± 5 | 19 ± 9 |

The data represents average values ± standard deviation
* Represent values statistically higher than control, $p < 0.05$ versus 316 L Stainless Steel control group.

Effect of VAC on Rats of Advanced Age

The effect of local vanadium therapy on healing of femur fractures in normal (non-diabetic) rats was measured by torsional mechanical testing. At four weeks post-fracture, fractured femurs from the rats of advanced age (190-195 days of age) treated with VAC had greater mechanical properties than the fractured femurs from the control group. When the mechanical parameters of the fractured femora were non to the intact, contralateral femora, percent maximum torque to failure (saline group vs. 1.5 mg/kg VAC group $p<0.05$ was significantly greater in the local vanadium treated groups when compared to the saline group (Table 16).

Healing was assessed by radiographic examination and quantified by mechanical testing. Local VAC treatment improved radiographic appearance and significantly increased the mechanical strength of fractured femurs. At four weeks post-fracture, the average percent maximum torque to failure of the fractured femora for 1.5 mg/kg VAC was significantly 76 percent greater (44.0% of contralateral vs. 25.0%), compared to the untreated saline group (Table 16), The data indicate that local VAC treatment enhanced bone regeneration during fracture healing even in a population of advanced age.

TABLE 16

Four weeks post-fracture mechanical testing with local vanadium (VAC) in rats of advanced age (Age: 190-195 days)

Fractured Femur Values

|  | Maximum Torque to Failure (Nmm) | Maximum Torsional Rigidity (Nmm$^2$/rad) | Effective Shear Modulus (MPa) | Effective Shear Stress (MPa) | Mean Angle at Failure (degrees) |
|---|---|---|---|---|---|
| Saline Control (n = 3) | 220 ± 76 | $4.2 \times 10^4 \pm 1.7 \times 10^4$ | $2.2 \times 10^3 \pm 1.5 \times 10^3$ | 36 ± 5 | 6 ± 3 |
| 1.5 mg/kg VAC (n = 4) | 324 ± 83 | $3.0 \times 10^4 \pm 1.8 \times 10^4$ | $1.3 \times 10^3 \pm 1.3 \times 10^3$ | 43 ± 17 | 12 ± 4 |

Fractured Femur Values Normalized to the Contralateral (Intact) Femur

|  | Percent Maximum Torque to Failure | Percent maximum Torsional Rigidity | Percent Effective Shear Modulus | Percent Effective Shear Stress |  |
|---|---|---|---|---|---|
| Saline Control (n = 3) | 2.5 ± 7 | 62 ± 19 | 24 ± 10 | 15 ± 7 | NA |
| 1.5 mg/kg VAC (n = 4) | 44 ± 10 * | 56 ± 37 | 16 ± 18 | 16 ± 4 | NA |

Figure 11:
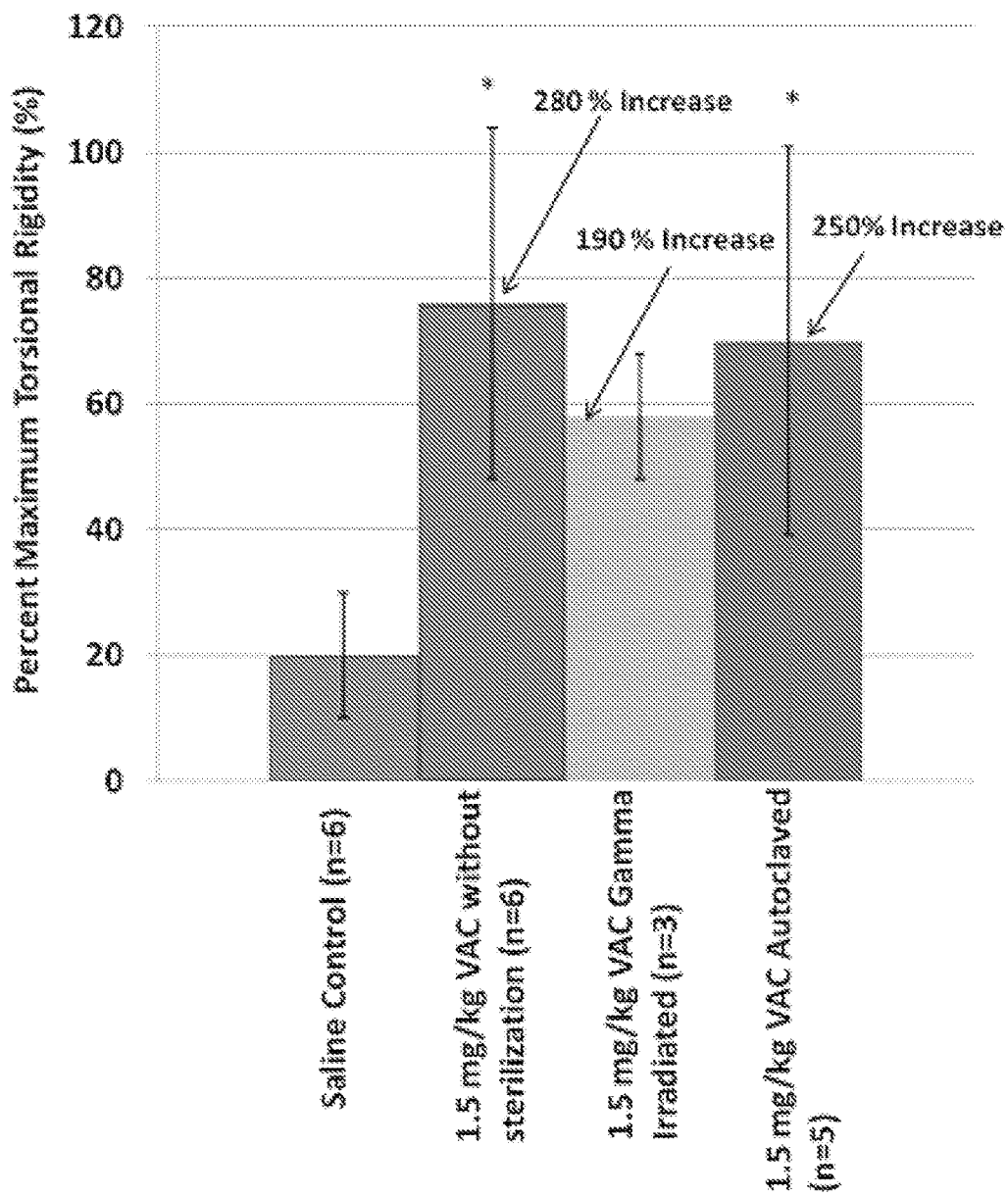
FIG. 11 illustrates 4-week mechanical testing of treatment with VAC with or without sterilization (normalized to intact femora). The data represents average values±standard deviation. * Represent values statistically higher than control, $p<0.05$ versus saline control.

The data represents average values ± standard deviation
* Represents values statistically higher than saline control, p < 0.05 versus saline control.
Student t-test between 2 groups The effect of local vanadium therapy on healing of femur fractures in normal (non-diabetic) rats was measured by torsional mechanical testing. At four weeks post-fracture, fractured femurs from the rats treated with VAC had greater mechanical properties than the fractured femurs from the control group, even if the VAC solution was autoclaved or gamma irradiated prior to administration (FIG. 11, Table 17). For the 1.5 mg/kg VAC group without sterilization, the maximum torque to failure (saline group vs. 1.5 mg/kg VAC group without sterilization p<0.05) and torsional rigidity (saline group vs. 1.5 mg/kg VAC group without sterilization p<0.05) were significantly greater than the saline control group. For the 1.5 mg/kg VAC autoclaved VAC group, the torsional rigidity (saline group vs. 1.5 mg/kg autoclaved VAC group p<0.05) was significantly greater than the saline control group (Table 17). When the mechanical parameters of the fractured femora were normalized to the intact, contralateral femora, percent torsional rigidity (saline group vs. 1.5 mg/kg VAC group without sterilization p<0.05, saline group vs. 1.5 mg/kg autoclaved VAC group p<0.05), and shear modulus (saline group vs. 1.5 mg/kg VAC group without sterilization p<0.05) were significantly greater in the local vanadium treated groups when compared to the saline group (Table 17).

TABLE 17

Four weeks post-fracture mechanical testing with local vanadium (VAC) without a Carrier

|  | Maximum Torque to failure (Nmm) | Maximum Torsional Rigidity (Nmm$^2$/rad) | Effective Shear Modulus (MPa) | Effective Shear Stress (MPa) |
|---|---|---|---|---|
| Saline Control (n = 6) | 161 ± 48 | $9.9 \times 10^3 \pm 4.7 \times 10^3$ | $2.6 \times 10^2 \pm 1.1 \times 10^2$ | 17 ± 4 |
| 1.5 mg/kg VAC without sterilization (n = 6) | 329 ± 117 * | $3.5 \times 10^4 \pm 1.7 \times 10^{4*}$ | $2.5 \times 10^3 \pm 2.4 \times 10^3$ | 69 ± 59 |
| 1.5 mg/kg VAC Gamma Irradiated (n = 3) | 276 ± 79 | $2.6 \times 10^4 \pm 3.7 \times 10^3$ | $7.9 \times 10^4 \pm 9.4 \times 10^2$ | 28 ± 4 |
| 1.5 mg/kg VAC Autoclaved (n = 5) | 292 ± 83 | $3.4 \times 10^4 \pm 1.5 \times 10^{4*}$ | $9.6 \times 10^2 \pm 7.8 \times 10^2$ | 26 ± 16 |

TABLE 17-continued

Four weeks post-fracture mechanical testing with local vanadium (VAC) without a Carrier Fractured Femur Values Normalized to the Contralateral (Intact) Femur

|  | Percent maximum torque to failure | Percent maximum torsional rigidity | Percent Effective Shear Modulus | Percent Effective Shear Stress |
|---|---|---|---|---|
| Saline Control (n = 6) | 27 ± 18 | 20 ± 10 | 4 ± 2 | 10 ± 5 |
| 1.5 mg/kg VAC without sterilization (n = 6) | 5 ± 78 | 76 ± 28* | 23 ± 12* | 26 ± 16 |
| 1.5 mg/kg VAC Gamma Irradiated (n = 3) | 50 ± 18 | 58 ± 10 | 9 ± 2 | 14 ± 5 |
| 1.5 mg/kg VAC Autoclaved (n = 5) | 47 ± 12 | 70 ± 31* | 15 ± 10 | 14 ± 7 |

The data represents average values ± standard deviation
*Represents values statistically higher than saline control, p < 0.05 versus saline control.
One-way ANOVA between 4 groups with Holm-Sidak post-hoc analysis.

Healing was assessed by radiographic examination and quantified by mechanical testing. Local VAC treatment improved radiographic appearance and significantly increased the mechanical strength of fractured femurs. At four weeks post-fracture, the average percent maximum torsional rigidity values for 1.5 mg/kg VAC without sterilization and following the autoclave process were significantly greater, with non-sterile VAC; 2.8 times greater (76.0% of contralateral vs. 20.0%), and autoclaved VAC; 2.5 times greater (70.0% of contralateral vs. 20.0%) compared to the saline control group. Percent shear modulus values for 1.5 mg/kg VAC without sterilization was significantly greater; 4.8 times greater (23.0% of contralateral vs. 4.0%) compared to the saline control group. The data indicate that local VAC treatment enhanced bone regeneration during fracture healing and indicates that effective sterilization techniques that may affect the stability and bioactivity of proteins, do not significantly alter the bioactivity of VAC.

Figure 12:
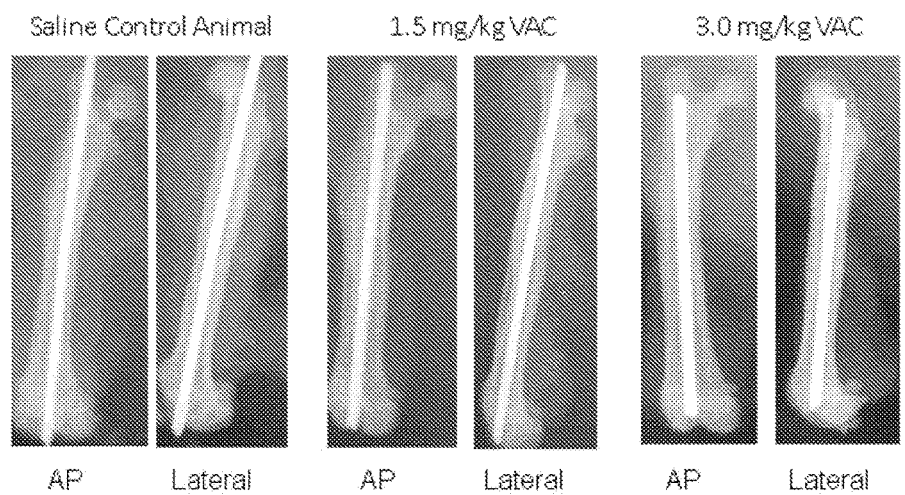
FIG. 12 illustrates the effect of local vanadium therapy on long-term healing of femur fractures in normal (non-diabetic) rats, measured by radiographic analysis.

The effect of local vanadium therapy on healing of femur fractures in normal (non-diabetic) rats was measured by radiographic analysis. At twelve weeks post-fracture, fractured femurs from the rats treated with both low (1.5 mg/kg) and high (3.0 mg/kg) VAC had no evidence of ectopic bone formation, following resolution of the induced fracture (FIG. 12). Femora treated with local VAC demonstrated normal remodeling suggesting no evidence of a toxic/carcinogenic effect of VAC throughout fracture healing. The above data have demonstrated an effective VAC therapeutic dosage range 0.5 to 3.0 mg/Kg, which resulted in two to three-fold increase in mechanical parameter of torsion.

Comparison with Existing Therapies

Figure 13:
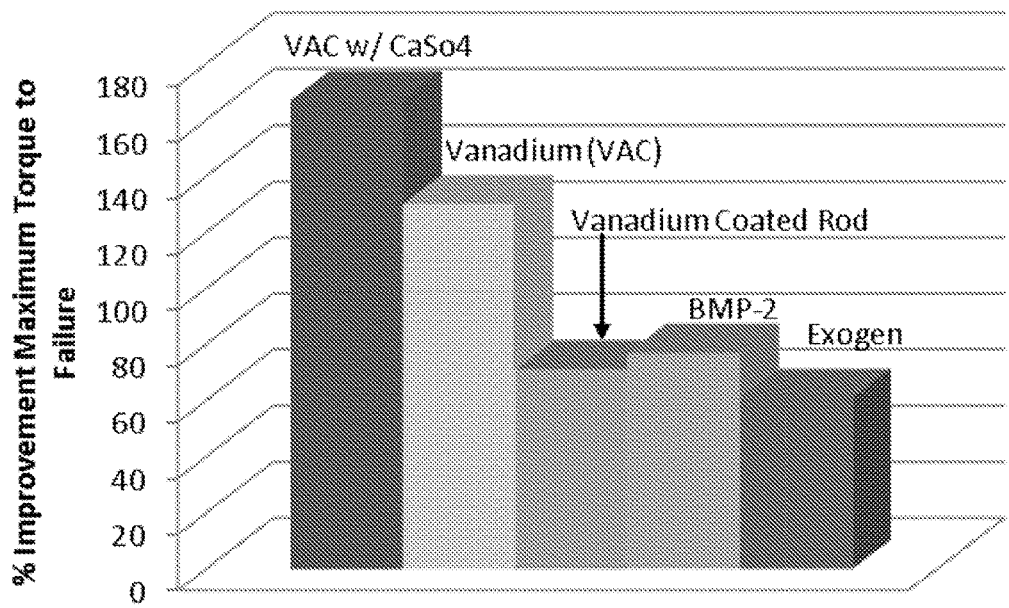
FIG. 13 illustrates comparison of local VAC treatment with current BMP2 and Exogen therapies.

The chart in FIG. 13 compares the vanadium technologies with the currently approved products (BMP-2 and Exogen) for fracture healing. Each of these studies examined the effectiveness of a therapeutic adjunct on femur fracture healing by measuring the maximum torque to failure at the same timepoint (four weeks). Specifically the following were compared: (1) a single percutaneous dose (0.25 mg/kg) of VAC with the calcium sulfate (CaSO$_4$) vehicle (red); (2) a single percutaneous dose (1.5 mg/kg) of VAC without a vehicle (blue); (3) a 316L stainless steel k-wire surface modified with vanadium (a process called vanadium packboriding), implanted into the intramedullary canal of the femur (green); (4) BMP-2 study used a single percutaneous dose of BMP-2 (80 μg) with buffer vehicle (orange); and (5) Exogen study used varying exposure periods of ultrasound treatment (20 mins/day). The most effective duration (25 days) is shown in dark blue.

Thus, the results have demonstrated, among others, (a) that the use of vanadium compounds (such as VAC) alone or as part of a formulation with an orthopedic carrier (CaSO4 for example) that is applied directly to the site of fracture; and (b) that the use of orthopedic implants (pedicle screws, plates, rods, wires, etc.) where the surface has been modified with vanadium via known thermal processing techniques. As an insulin-mimetic adjunct, vanadium compounds can be used to accelerate bone regeneration by stimulating insulin signaling at the fracture site. Local VAC targets the beta-subunit of the insulin signaling receptor. The presence of the insulin mimetic also enhances cartilage and mineralized tissue formation. Our laboratory data demonstrated that VAC treatment significantly increases cell proliferation within the subperiosteal region of the fracture callus (seven and ten days post-fracture). This translates into significantly higher percent cartilage within the fracture callus, (seven and ten days post-fracture). The percent mineralized tissue for local VAC treated rat animal models was significantly higher than controls after 21 days. This accelerated progression of the bone healing process results in significantly enhanced mechanical testing parameters for VAC treated animals after four and five weeks, compared to controls.

Example 4

Insulin Mimetics Enhancing Spinal Fusion

Increased fusion rates were observed in a rat posterolateral lumbar spinal fusion model when treated with a time-released insulin implant in comparison with controls. The effects of insulin-mimetic agents were analyzed as an adjunct to spinal fusion in the rat posterolateral lumbar fusion model. Vanadyl acetylacetonate (VAC) or Zinc was made into a pellet with Calcium Sulfate, and applied to the fusion bed with autograft in a rat posterolateral lumbar fusion. These results were compared with a control group treated with autograft and a palmitic acid pellet.

Study Design

The protocol was approved by the animal Institutional Care and Use Committee at UMDNJ-New Jersey Medical School. Fifty skeletally mature Sprague-Dawley rats weighing approximately 500 grams each underwent posterolateral intertransverse lumbar fusions with iliac crest mop-aft from L4-L5 utilizing a Wiltse-type approach. After exposure of the transverse processes and high-speed burr decortication, one of five pellets were added to the fusion site: a low dose Vanadium Calcium Sulfate pellet (0.75 mg/kg), a high dose Vanadium Calcium Sulfate pellet (1.5 mg/kg), a low dose Zinc Calcium Sulfate pellet (0.5 mg/kg), a high dose Zinc Calcium Sulfate pellet (1.0 mg/kg), and a control of micro-recrystallized palmitic acid pellet. An equal amount of iliac crest autograft (approximately 0.3 g per side) was harvested and implanted with each pellet. The rats were sacrificed at eight weeks, and spines were harvested, removed of soft tissue, and tested by manual palpation, radiographs and MicroCT. All outcome parameters were independently reviewed by two separate individuals in a blinded manner and the lower grade of fusion was accepted when there was a discrepancy.

Surgical Procedure

Figure 14:
FIG. 14 illustrates that the transverse processes of L4-L5 were cleaned of soft tissue, and decorticated with a high-speed burr.
Figure 15:
FIG. 15 illustrates that the crushed autograft was then spread over and between the transverse processes at the appropriate level (L4-L5). An equivalent amount of implant or blank was incorporated into the autograft bed.

After obtaining general anaesthesia with intraperitoneal Ketamine (40 mg/kg) and Xylazine (5 mg/kg), the lumbar region of the rat was shaved and cleansed with povidone iodine soaked gauze. A dorsal midline incision was made from L3 to the sacrum. Two paramedian incisions were made through the lumbar fascia 5 mm from the midline. Dissection was taken to the iliac crest, and approximately 0.3 g of bone was harvested with small rongeurs. The harvested autograft was measured on a sterile scale in order to obtain 0.3 g per side. Blunt dissection was carried down posterolaterally, reflecting the paraspinal muscles lateral to the facet joints on each side. The reflected paraspinal muscles were held in place with retractors. The transverse processes of L4-L5 were cleaned of soft tissue, and decorticated with a high-speed burr (FIG. 14). The crashed autograft was then spread over and between the transverse processes at the appropriate level (L4-L5). An equivalent amount of implant, or blank was incorporated into the autograft bed (FIG. 15). Retractors were removed and the paraspinal muscles were allowed to cover the fusion bed. The dorsal lumbar fascia was closed using a running 4-0 resorbable suture and the skin was closed with interrupted 4-0 resorbable sutures. The surgical site was treated with antibiotic ointment, and the rats were given a dose of Enrofloxacin antibiotic (10 mg/kg). Radiographs were taken immediately after surgery. Blood glucose levels were taken before surgery, and 12 and 24 hours after surgery. See Table 18.

TABLE 18

Systemic blood glucose levels (mg/dL)

| Group | Before surgery | 12 hours | 24 hours |
| --- | --- | --- | --- |
| Controls | | | 91.4 |
| VAC-low | 103.5 | 213.4 | 117.7 |

TABLE 18-continued

Systemic blood glucose levels (mg/dL)

| Group | Before surgery | 12 hours | 24 hours |
| --- | --- | --- | --- |
| VAC-high | 102.9 | 153.2 | 90.7 |
| Zn-low | 106.0 | 122.8 | 101.8 |
| Zn-high | 109.3 | 120.0 | 89.0 |

Pellet Preparation

In order to prepare the pellets, 0.2 mL of each stock solution will be mixed with 0.4 g of $CaSO_4$ to obtain the appropriate consistency of the carrier in a 1 mL syringe. It will then be injected into 2 mm diameter clear Tygon laboratory tubing and allowed to harden overnight.

Once set, pellets will be sectioned into 7 mm pieces and autoclaved (to sterilize), prior to implantation.

Assumption: Weight of SD rat=0.45 kg

| | Vn (0.75 mg/kg) | Vn (1.5 mg/kg) | Zn (0.5 mg/kg) | Zn (1.0 mg/kg) |
| --- | --- | --- | --- | --- |
| Mass of treatment for each rat | 0.338 mg | 0.675 mg | 0.225 mg | 0.45 mg |

In order to prepare the stock solution, the volume of solution in each pellet will be calculated by using the volume ratio of solution to mixture.

Volume of $CaSO_4$ in each mixture $$D\ CaSO_4 = 2.96\ \text{g/cm}^3$$

$$(0.4\text{g\_CaSO}_4) / \left(2.96\frac{\text{g}}{\text{cm}^3}\right) = 0.135\ \text{cm}^3 = 0.135\ \text{mL}$$

Volume of mixture and ratio
0.135 mL $CaSO_4$+0.2 mL solution=0.335 mL mixture
0.2 mL solution/0.335 mL mixture×100%=59.7% solution per mixture
Volume of each pellet, 1 mm radius, 7 mm height
$V = \pi r^2 h$, $=\pi(1\ \text{mm})^2(7\ \text{mm}) = 22\ \text{mm}^3 = 0.022\ \text{mL}$
Volume of solution in each pellet
0.022 mL×59.7%=0.0131 mL solution per pellet
Stock Solution (10 mL)
Because bilateral surgery is performed, mass of treatment (X) must be halved for each pellet.

$$\left(\left(\frac{X}{2}\right) / 0.0131\ \text{mL}\right) \times 10$$

| | Vn (0.75 mg/kg) | Vn (1.5 mg/kg) | Zn (0.5 mg/kg) | Zn (1.0 mg/kg) |
| --- | --- | --- | --- | --- |
| Mass of treatment in each stock solution (10 ml) | 129.0 mg | 258.0 mg | 85.9 mg | 171.8 mg |

Radiographic Analysis

Posteroanterior radiographs at 35 kV for 90 seconds were taken at eight weeks after sacrifice and harvest. All soft tissue was removed prior to radiographic exam. Two blinded independent observers graded the radiographs as solid fusion mass bilaterally (A), unilateral fission mass (B), small fission mass bilaterally (C), and graft resorption (D), based on previously published radiographic scales. See Table 19.

TABLE 19

Radiographs

| Group | A | B | C | D | Kappa | P Value |
|---|---|---|---|---|---|---|
| Controls (n = 9) | 2 | 3 | 1 | 3 | 0.297 | |
| VAC-low (n = 10) | 3 | 3 | 0 | 4 | 0.583 | 0.807 |
| VAC-high (n = 10) | 5 | 3 | 1 | 1 | 0.667 | 0.270 |
| Zn-low (n = 10) | 7 | 1 | 2 | 0 | 0.512 | 0.066 |
| Zn-high (n = 10) | 7 | 3 | 0 | 0 | 1.0 | 0.050 |

Figure 16:
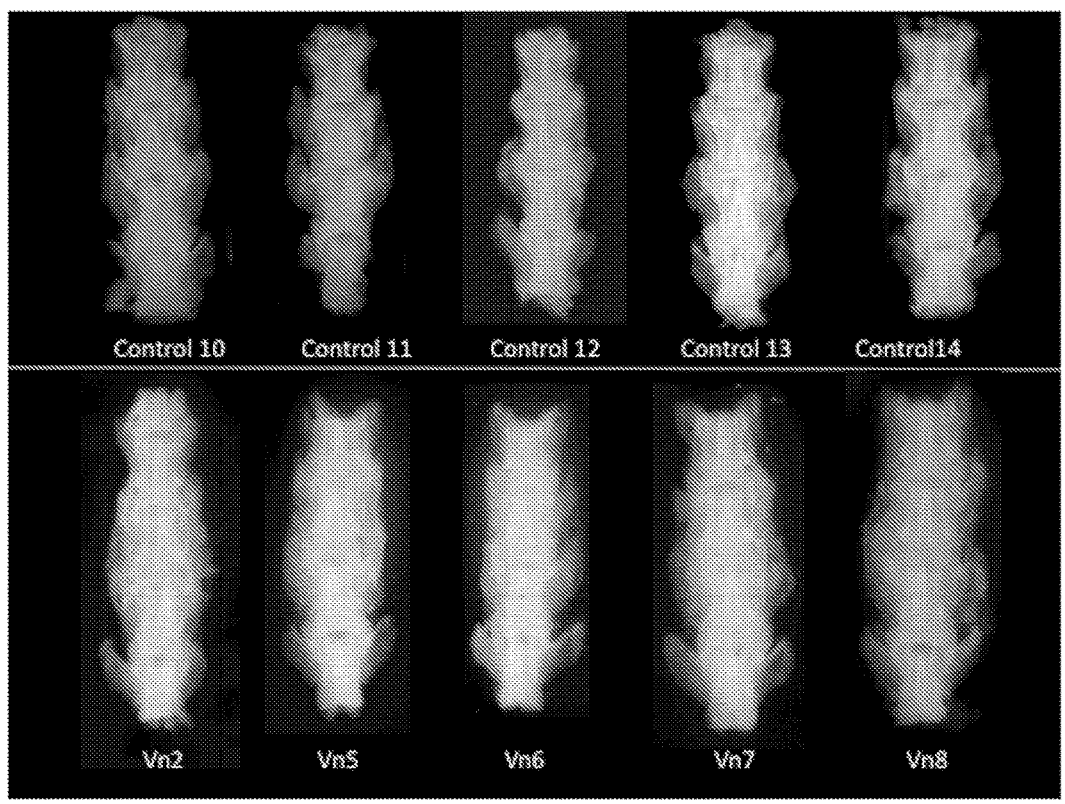
FIG. 16 illustrates radiographs of the vanadium-treated spines in the rat model in comparison with those in the control group.

A = solid fusion mass bilaterally
B = unilateral fusion mass
C = small fusion mass bilaterally
D = Graft resorption Based on radiographs (FIG. 16), in the high dose vanadium group 5/10 had solid fusion mass bilaterally, 3/10 had unilateral fusion, 1/10 had small fusion mass bilaterally, and 1/10 had graft resorption. The low dose vanadium group had 3/10 solid fusion mass bilaterally, 3/10 had unilateral fusion, 0/10 had small fusion mass bilaterally, and 4/10 had graft resorption. The high dose zinc, group had 7/10 solid fusion mass bilaterally, 3/10 had unilateral fusion, 0/10 had small fusion mass bilaterally, and 0/10 had graft resorption. The low dose zinc group had 7/10 solid fusion mass bilaterally, 1/10 had unilateral fusion, 2/10 had small fusion mass bilaterally, and 0/10 had graft resorption. The control group had 2/9 solid fusion mass bilaterally, 3/9 unilateral fusion, 1 small fusion mass bilaterally, and 3/9 had graft resorption.

Manual Palpation

After removal of all soft tissue, two blinded independent observers manually palpated and stressed across the fusion site (L4-L5). Specimens were graded as fused (A), partially fused (B), and not fused (C). See Table 20.

TABLE 20

Manual palpation

| Group | A | B | C | Kappa | P Value |
|---|---|---|---|---|---|
| Controls (n = 9) | 0 | 1 | 8 | 0.156 | |
| VAC-low (n = 10) | 1 | 4 | 5 | 0.130 | 0.072 |
| VAC-high (n = 10) | 6 | 2 | 2 | 0.412 | 0.002 |
| Zn-low (n = 10) | 3 | 4 | 3 | 0.565 | 0.055 |
| Zn-high (n = 10) | 4 | 1 | 5 | 0.306 | 0.008 |

A = fused
B = partially fused
C = not fused

Based on manual palpation in the high dose Vanadium group 6/10 had solid fusion, 2/10 were partially fused, and 2/10 were not fused. In the low dose vanadium group, 1/10 had solid fusion, 4/10 were partially fused, and 5/10 were not fused. In the high dose Zinc group, 4/10 had solid fusion, 1/10 had partially fused, and 5/10 were not fused. In the low dose Zinc group, 3/10 had solid fusion, 4/10 had partially fused, and 3/10 were not fused. In the control group, 0/9 had solid fusion, 1/9 had partially fused, and 8/9 were not fused.

Micro CT Analysis

TABLE 21

MicroCT

| Group | Mean Bone Volume mm$^3$ | Std Dev | P value |
|---|---|---|---|
| Table 21a | | | ANOVA p = 0.006 |
| Vn high dose (n = 10) | 170.8 | 37.1 | <0.01 vs control |
| Vn low dose (n = 10) | 167.4 | 23.5 | <0.05 vs control |
| Controls (n = 9) | 126.7 | 26.3 | |
| Table 21b | | | ANOVA p = 0.002 |
| Zn high dose (n = 10) | 172.7 | 26.4 | <0.01 vs control |
| Zn low dose (n = 10) | 172.9 | 31.6 | <0.01 vs control |
| Controls (n = 9) | 126.7 | 26.3 | |

Based on MicroCT analysis, the mean bone volume of the L4/L5 transverse processes and fusion mass for controls was 126.7 mm$^3$. In the high dose Vanadium group there was 170.8 mm$^3$, and in the low dose Vanadium group there was 167.4 mm$^3$. The high dose Zinc group had a mean of 172.7 mm$^3$, and the low dose Zinc group had a mean of 172.9 mm$^3$. Differences between each experimental group versus controls were significant (see Table 21).

Statistical Analysis

A Mann-Whitney Rank Test was performed for analysis of radiographs and manual palpation. Kappa values were calculated for inter-rater agreement. ANOVA was performed for amt of new bone limitation as per micro CT with secondary test using Holm Sidak test. Statistical analysis was performed using SigmaStat.

Of the 50 animals, one of the control rats died on postoperative day one, likely due to anaesthesia. The remaining 49 rats had no complications and were sacrificed as planned (0.02% perioperative mortality rate).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims. All references cited hereby are incorporated by reference in their entirety.

What is claimed is:

1. An orthopedic or spinal implant, comprising at least one bone-contacting surface comprising an active ingredient consisting of an insulin-mimetic organic acid zinc salt or composition thereof.

2. The orthopedic or spinal implant of claim 1, wherein the orthopedic implant is selected from the group consisting of screws, plates, rods, k-wires, pins, hooks, anchors, intramedullary devices, pedicle screws, pedicle hooks, spinal fusion cages, spinal fusion plates, prostheses, and porous metal.

3. The orthopedic or spinal implant of claim 2, wherein said implant is made from a metal selected from the group consisting of titanium, alloys thereof, tantalum, alloys thereof, cobalt chrome alloys, steel alloys, and combinations thereof.

4. The orthopedic or spinal implant of claim 3, wherein said steel alloy is a stainless steel.

5. The orthopedic or spinal implant of claim 2, wherein said implant is made from a polymeric material.

6. The orthopedic or spinal implant of claim 5, wherein said polymeric material comprises a polymer selected from polyglycolic acid (PGA), poly(lactic-co-glycolic acid) (PLGA), polylactic acid (PLA), polycaprolactone (PCL), polyether ether ketone (PEEK), polyethylene terephthalate (PET), polypropylene (PP), polycarbonates (PC), poly(ortho esters) (POEs), and combinations thereof.

* * * * *